(12) United States Patent
Piraka

(10) Patent No.: US 11,517,345 B2
(45) Date of Patent: Dec. 6, 2022

(54) SNARE ASSEMBLY PORTION, AN ENDOSCOPIC CATHETER ASSEMBLY AND A METHOD FOR UTILIZING THE SAME

(71) Applicant: Henry Ford Health System, Detroit, MI (US)

(72) Inventor: Cyrus R. Piraka, Northville, MI (US)

(73) Assignee: Henry Ford Health System, Detroit, MI (US)

( * ) Notice: Subject to any disclaimer, the term of this patent is extended or adjusted under 35 U.S.C. 154(b) by 191 days.

(21) Appl. No.: 16/073,249

(22) PCT Filed: Jan. 20, 2017

(86) PCT No.: PCT/US2017/014411
§ 371 (c)(1),
(2) Date: Jul. 26, 2018

(87) PCT Pub. No.: WO2017/132065
PCT Pub. Date: Aug. 3, 2017

(65) Prior Publication Data
US 2019/0029706 A1 Jan. 31, 2019

Related U.S. Application Data

(60) Provisional application No. 62/287,752, filed on Jan. 27, 2016.

(51) Int. Cl.
| | |
|---|---|
| *A61B 17/3205* | (2006.01) |
| *A61B 17/221* | (2006.01) |
| *A61B 17/32* | (2006.01) |
| *A61B 17/3209* | (2006.01) |
| *A61B 17/34* | (2006.01) |
| *A61B 17/22* | (2006.01) |
| *A61B 17/00* | (2006.01) |
| *A61B 18/14* | (2006.01) |

(52) U.S. Cl.
CPC ........ *A61B 17/32056* (2013.01); *A61B 17/22* (2013.01); *A61B 17/221* (2013.01); *A61B 17/32* (2013.01); *A61B 17/3209* (2013.01); *A61B 17/320016* (2013.01); *A61B 17/34* (2013.01); *A61B 2017/00269* (2013.01); *A61B 2017/00358* (2013.01); *A61B 2018/141* (2013.01)

(58) Field of Classification Search
CPC ....... A61B 17/22; A61B 17/221; A61B 17/32; A61B 17/320016; A61B 17/32056; A61B 17/3209; A61B 17/34; A61B 2017/00269; A61B 2017/00358; A61B 2018/141
See application file for complete search history.

(56) References Cited

U.S. PATENT DOCUMENTS

| | | | | |
|---|---|---|---|---|
| 6,328,730 B1 * | 12/2001 | Harkrider, Jr. | ..... | A61B 17/3421 600/130 |
| 6,770,066 B1 * | 8/2004 | Weaver | ............. | A61M 25/0026 604/508 |
| 2004/0059345 A1 * | 3/2004 | Nakao | .................. | A61B 17/221 606/113 |

(Continued)

*Primary Examiner* — Sarah A Simpson
(74) *Attorney, Agent, or Firm* — Honigman LLP; Fernando Alberdi; Jonathan P. O'Brien

(57) ABSTRACT

An endoscopic catheter assembly including a catheter portion is disclosed. The catheter portion includes a proximal portion and a distal portion. The catheter portion includes a tube-shaped body defining a passage extending therethrough.

3 Claims, 24 Drawing Sheets

(56) References Cited

U.S. PATENT DOCUMENTS

| | | | |
|---|---|---|---|
| 2006/0253128 A1* | 11/2006 | Sekine | A61B 17/00234 606/139 |
| 2011/0087258 A1* | 4/2011 | Sluss | A61B 17/320016 606/170 |
| 2012/0209221 A1* | 8/2012 | Patterson | A61M 25/0021 604/284 |

* cited by examiner

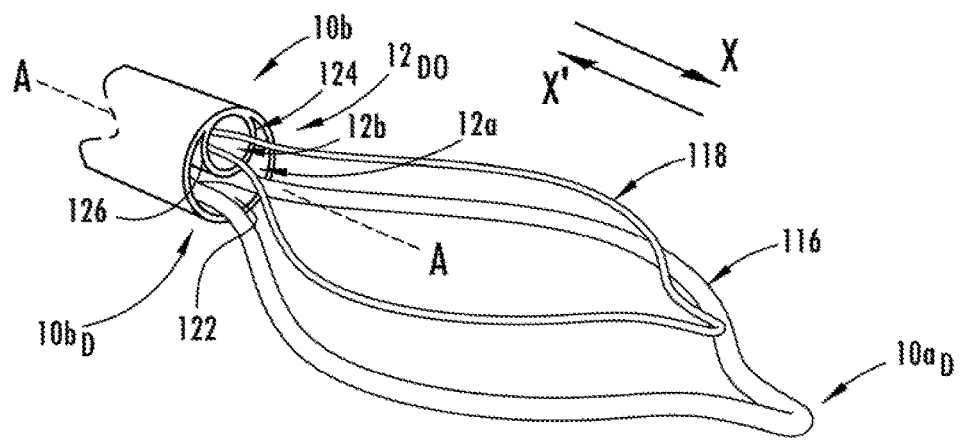
FIG. 13A
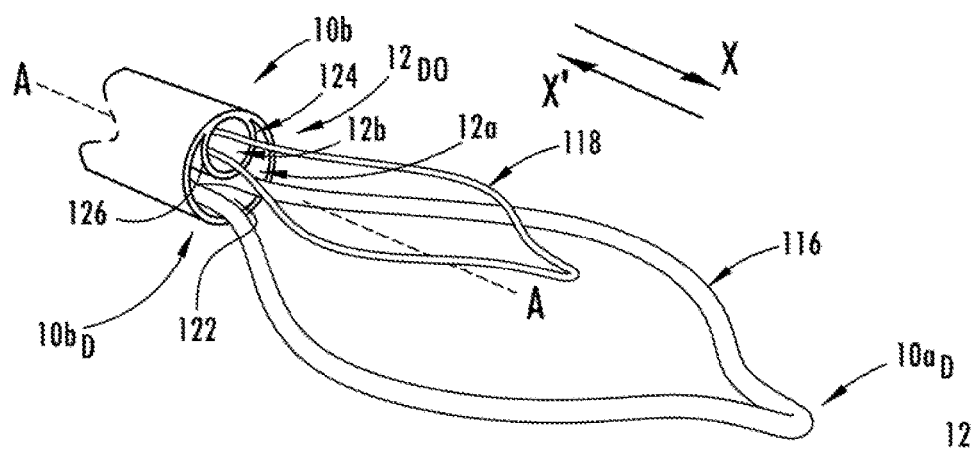
FIG. 13B
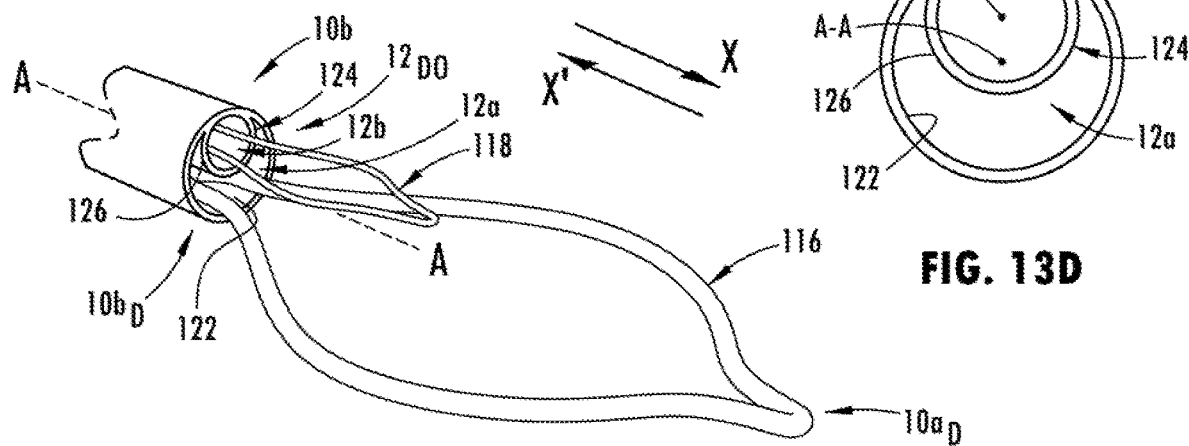
FIG. 13C
FIG. 13D

SNARE ASSEMBLY PORTION, AN ENDOSCOPIC CATHETER ASSEMBLY AND A METHOD FOR UTILIZING THE SAME

CROSS-REFERENCE TO RELATED APPLICATIONS

This application claims the benefit of and priority under 35 U.S.C. § 371 to Patent Cooperation Treaty application PCT/US2017/014411, filed Jan. 20, 2017, which claims the benefit of priority to U.S. Provisional Patent Application Ser. No. 62/287,752, filed Jan. 27, 2016, the entire contents of both disclosures, which are incorporated herein by reference in their entireties.

TECHNICAL FIELD

This disclosure relates to a snare assembly portion, an endoscopic catheter assembly and a method for utilizing the same.

BACKGROUND

Various medical devices are known in the art for performing tissue removal surgeries. In some instances, such medical devices may include, in part, a snare which removes a pathogenic tissue, for example, a cancer or precancerous tissue from surrounding healthy tissue.

While known medical devices have proven to be acceptable for various applications, such conventional medical devices are nevertheless susceptible to improvements that may enhance their overall performance and cost. Therefore, a need exists to develop improved medical devices and methodologies for forming the same that advance the art.

SUMMARY

An endoscopic catheter assembly is provided having a catheter portion. The catheter portion includes a proximal portion and a distal portion. The catheter portion includes a tube-shaped body defining a passage extending therethrough.

In one configuration, a radial wall extends across the passage formed by the catheter portion thereby connecting diametrically-opposing portions of an inner surface of the tube-shaped body defining the passage for bifurcating at least a portion of a length of the passage proximate a distal opening formed by the distal portion of the catheter portion into a first passage portion and a second passage portion.

In one configuration, the radial wall includes a cutting surface.

In one configuration, the cutting surface extends substantially perpendicularly from each of an upper surface of the radial wall and a lower surface of the radial wall for providing the radial wall with a dull or blunt cutting surface profile.

In one configuration, the cutting surface includes a first cutting surface portion that extends from an upper surface of the radial wall and a second cutting surface portion that extends from a lower surface of the radial wall. The first cutting surface portion is connected to the second cutting surface portion to define a blade edge. The first cutting surface portion and the second cutting surface portion extend away from the blade edge to define an angle for proving the radial wall with a sharp cutting surface profile.

In one configuration, the cutting surface is substantially aligned with and does not extend axially beyond the distal opening formed by the distal portion of the catheter portion.

In one configuration, the cutting surface extends axially beyond the distal opening formed by the distal portion of the catheter portion.

In one configuration, a tube-shaped member is arranged within the passage formed by the catheter portion thereby separating at least a portion of a length of the passage proximate a distal opening formed by the distal portion of the catheter portion into a first passage portion and a second passage portion. A portion of a circumference defining an outer surface of the tube-shaped member is joined directly to and extends from the inner surface. An axial center of the tube-shaped member is radially offset from a central axis extending through an axial center of the catheter portion.

In one configuration, a tube-shaped member is arranged within the passage formed by the catheter portion thereby separating at least a portion of a length of the passage proximate a distal opening formed by the distal portion of the catheter portion into a first passage portion and a second passage portion. The tube-shaped member is arranged in a radially spaced apart relationship with respect to the inner surface by four radially-projecting ribs that connect an outer surface of the tube-shaped member to the inner surface. The four radially-projecting ribs divide the first passage portion at least a portion of the length of the passage proximate the distal opening formed by the distal portion of the catheter portion into four first passage portions.

In one configuration, four radially-projecting ribs are arranged within the passage formed by the catheter portion thereby separating at least a portion of a length of the passage proximate a distal opening formed by the distal portion of the catheter portion into a first passage portion, a second passage portion, a third passage portion and a fourth passage portion. Each radially-projecting rib of the four radially-projecting ribs has a proximal end that is connected to an inner surface of the tube-shaped body defining the passage and a distal end that terminates at an axial center of the passage such that the distal end of each radially-projecting rib is connected to one another at the axial center of the passage.

In one configuration, the first passage portion contains and guides a portion of the length of the first snare shaft proximate the distal end of the first snare shaft and the first snare loop when the first snare loop is arranged in a retracted and collapsed orientation within the passage. The second passage portion contains and guides a portion of the length of the second snare shaft proximate the distal end of the second snare shaft and the second snare loop when the second snare loop is arranged in a retracted and collapsed orientation within the passage.

The details of one or more implementations of the disclosure are set forth in the accompanying drawings and the description below. Other aspects, features, and advantages will be apparent from the description and drawings, and from the claims.

DESCRIPTION OF DRAWINGS

FIGS. 13A-13C are perspective views of a distal portion of an exemplary snare subassembly portion and a distal portion of an exemplary catheter portion of an exemplary endoscopic catheter assembly.

FIG. 13D is an end view of the distal portion of the exemplary snare subassembly portion and the distal portion of the exemplary catheter portion of the exemplary endoscopic catheter assembly of FIGS. 13A-13C.

Like reference symbols in the various drawings indicate like elements.

DETAILED DESCRIPTION

Figure 1:
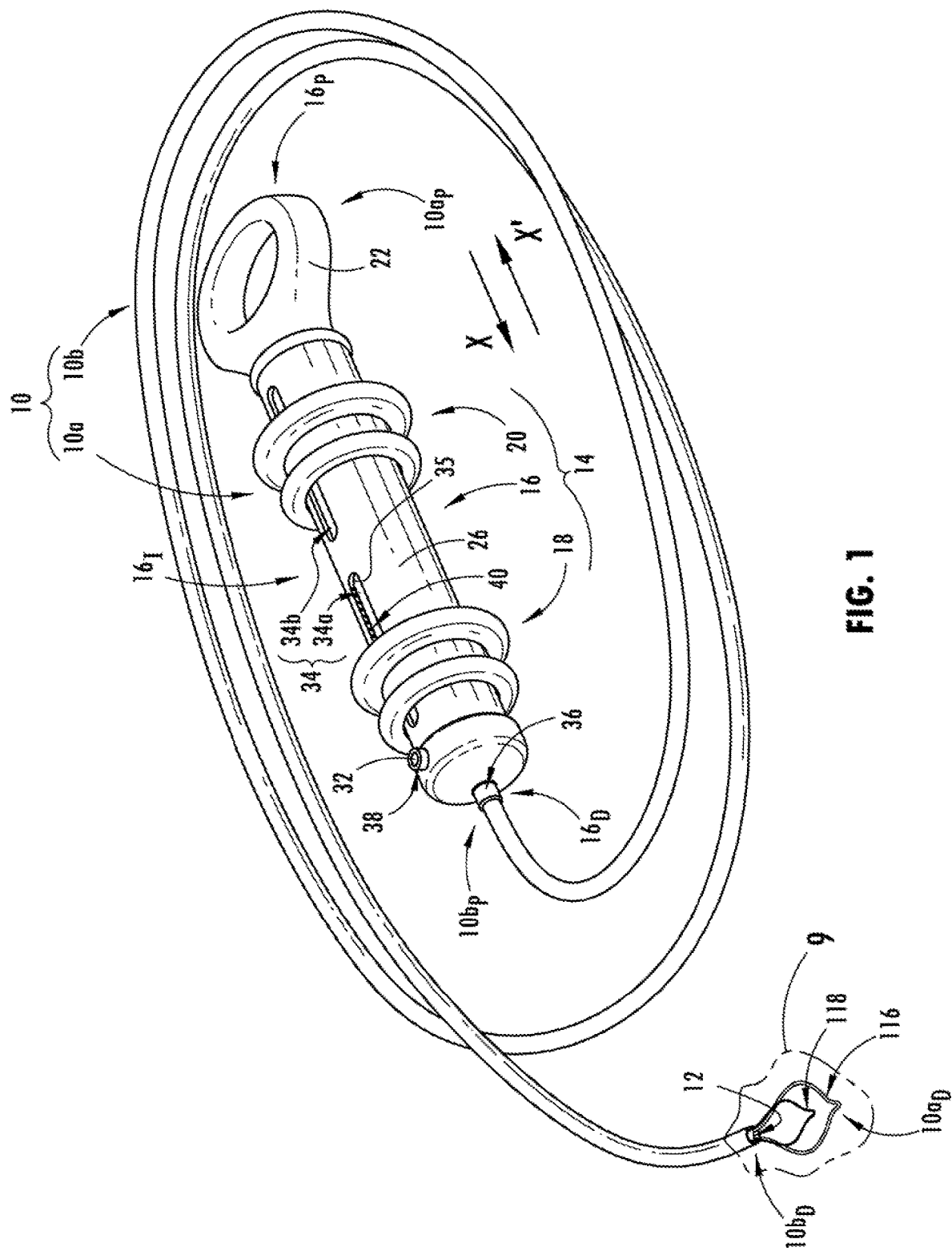
FIG. 1 is a perspective view of an endoscopic catheter assembly.

Referring to FIG. 1, an exemplary endoscopic catheter assembly is shown generally at 10. The endoscopic catheter assembly 10 includes a snare subassembly portion 10a and a catheter portion 10b. The snare assembly portion 10a is connected to a proximal portion $10b_P$ of the catheter portion 10b.

As seen in FIG. 1, the snare assembly portion 10a includes a proximal portion $10a_P$ and the distal portion $10a_D$. The snare assembly portion 10a defines an actuator 14 of the endoscopic catheter assembly 10. The actuator 14 may include a handle body 16, a first plunger 18 and a second plunger 20.

Referring to FIGS. 2-6, the handle body 16 includes a proximal portion $16_P$, a distal portion $16_D$ and an intermediate portion $16_I$ extending between the proximal portion $16_P$ and the distal portion $16_D$. The proximal portion $16_P$ of the handle body 16 may define a ring portion 22. A user may insert his/her finger through the ring portion 22 in order to improve a grip upon the proximal portion $16_P$ of the handle body 16 when a user axially displaces (according to the direction of arrows X, X') the first plunger 18 and/or the second plunger 20 relative to the handle body 16.

Figure 5:
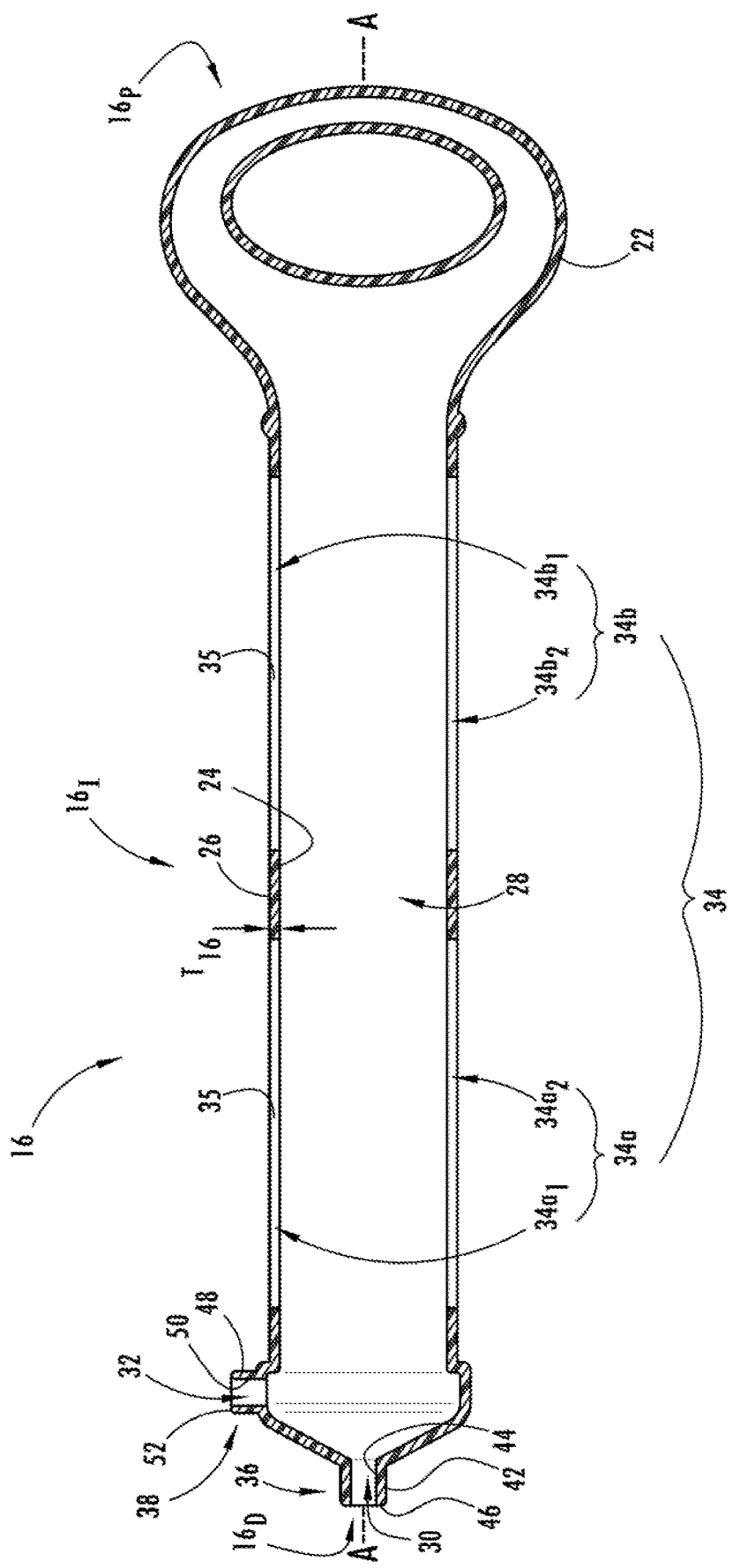
FIG. 5 is a cross-sectional view of a handle body of the snare subassembly portion according to line 5-5 of FIG. 2.

Referring to FIG. 5, the handle body 16 may be generally defined by an inner surface 24 and an outer surface 26. The handle body 16 may be defined by a thickness $T_{16}$ extending between the inner surface 24 and the outer surface 26.

The inner surface 24 may define the intermediate portion $16_I$ of the handle body 16 to be a substantially cylindrical, tube-shape member. The handle body 16 may have an interior cavity 28 that is defined by the inner surface 24 of the handle body 16. The interior cavity 28 may extend through the intermediate portion $16_I$ of the handle body 16.

Access to the interior cavity 28 may be permitted by a snare passage 30. The snare passage 30 may extend axially (relative a central axis, A-A) through the handle body 16. The snare passage 30 may be formed in the distal portion $16_D$ of the handle body 16.

Access to the interior cavity 28 may be permitted by a cautery device passage 32. The cautery device passage 32 may extend radially (relative the central axis, A-A) through the handle body 16. The cautery device passage 32 may be formed in the intermediate portion $16_I$ of the handle body 16.

Access to the interior cavity 28 may be permitted by at least one snare actuator passage 34. The at least one snare actuator passage 34 may extend radially (relative the central axis, A-A) through the handle body 16. The at least one snare actuator passage 34 may be formed in the intermediate portion $16_I$ of the handle body 16. The at least one snare actuator passage 34 may include a first snare actuator passage portion 34a and a second snare actuator passage portion 34b. The first snare actuator passage portion 34a permits the first plunger 18 to be movably-connected to the handle body 16 in axial directions (relative the central axis, A-A) according to the arrows X, X'. The second snare actuator passage portion 34b permits the second plunger 20 to be movably-connected to the handle body 16 in axial directions (relative the central axis, A-A) according to the arrows X, X'.

The first snare actuator passage portion 34a may include a first snare actuator passage $34a_1$ and a second snare actuator passage $34a_2$. The first snare actuator passage $34a_1$ and the second snare actuator passage $34a_2$ may be formed in the thickness $T_{16}$ of the handle body 16 in a diametrically-opposing relationship.

The second snare actuator passage portion 34b may include a first snare actuator passage $34b_1$ and a second snare actuator passage $34b_2$. The first snare actuator passage $34b_1$ and the second snare actuator passage $34b_2$ may be formed in the thickness $T_{16}$ of the handle body 16 in a diametrically-opposing relationship.

Figure 2:
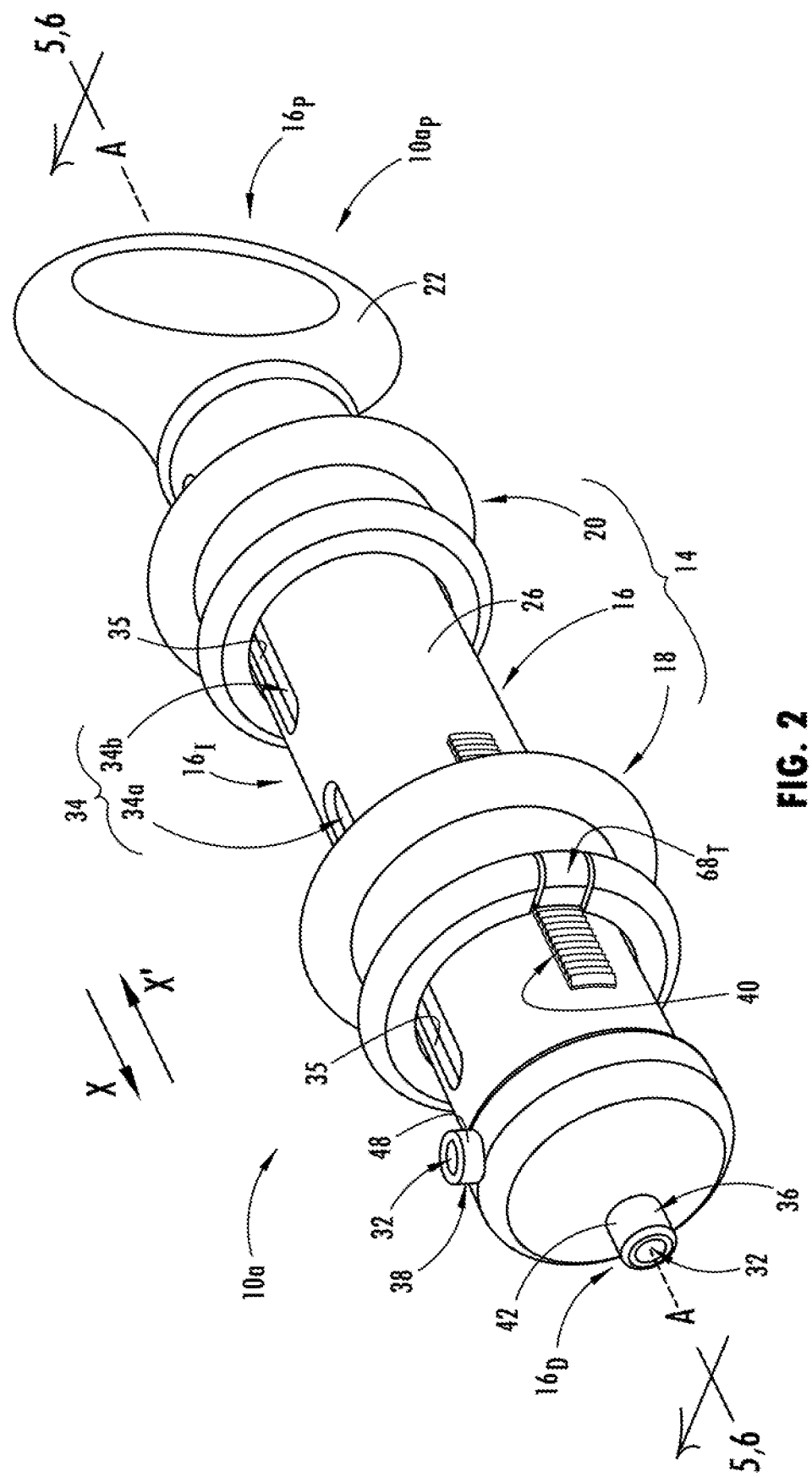
FIG. 2 is a perspective view of an exemplary snare subassembly portion of an endoscopic catheter assembly.
Figure 3:
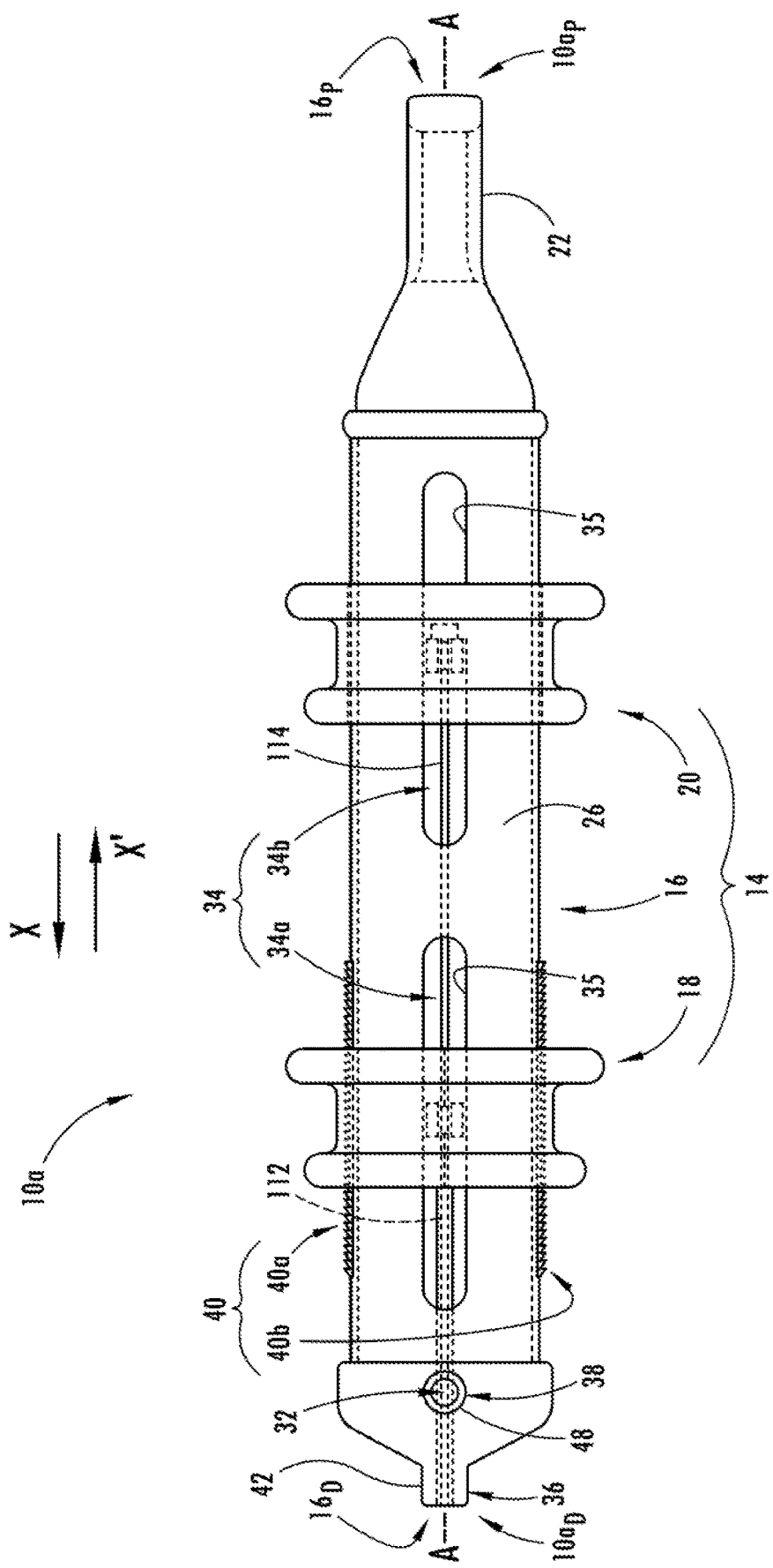
FIG. 3 is a top view of the snare subassembly portion of FIG. 2.
Figure 4:
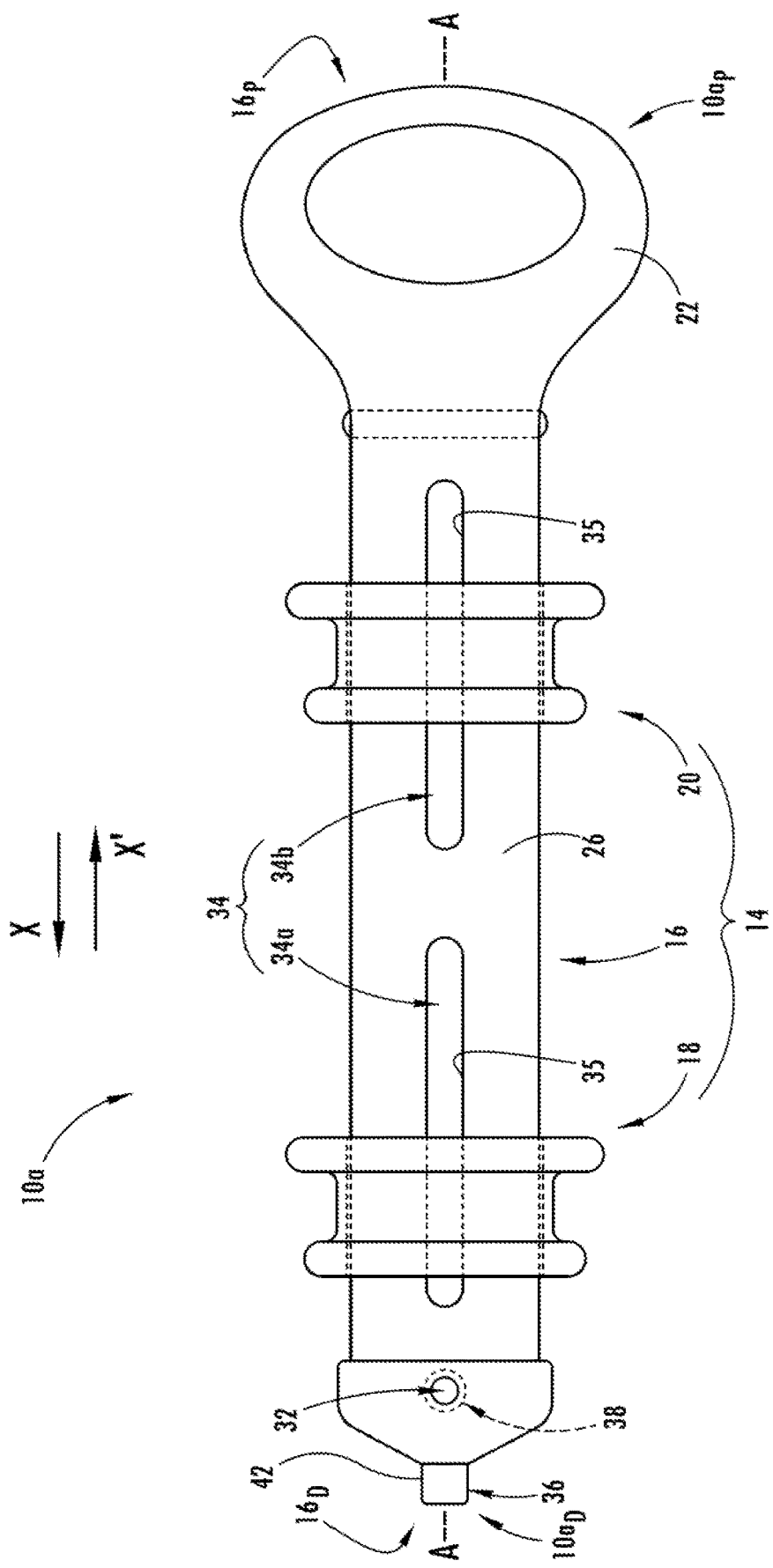
FIG. 4 is a side view of an exemplary snare subassembly portion.
Figure 10:
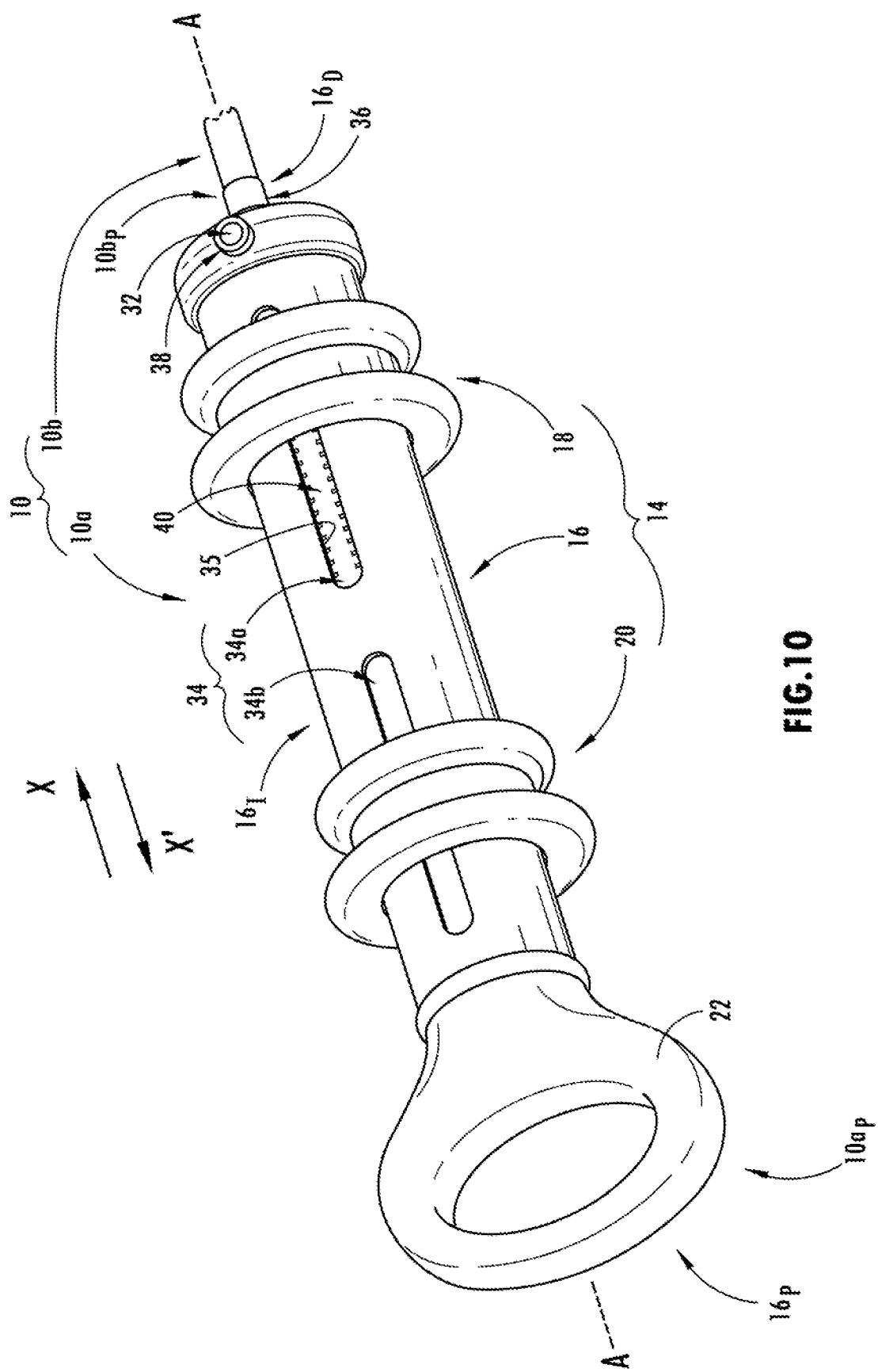
FIG. 10 is a perspective view of a portion of an exemplary endoscopic catheter assembly.

Referring to FIGS. 1-6, a first ring-shaped port 36 and a second ring-shaped port 38 may extend from the outer surface 26 of the handle body 16. Furthermore, as seen in FIGS. 1-3 and 10, the handle body 16 may include a frictional surface 40 such as, for example, as seen in FIGS. 2-3, a saw-tooth-shape series of "ratcheting teeth." Alternatively, in another example as seen in FIGS. 1 and 10, the frictional surface 40 may extend from a passage surface 35 defining one or more of the first snare actuator passage $34a_1$ and the second snare actuator passage $34a_2$ of the first snare actuator passage portion 34a; the passage surface 35 may connect the inner surface 24 of the handle body 16 to the outer surface 26 of the handle body 16. In the example seen in FIGS. 2-3, the frictional surface 40 defined by the saw-tooth-shape series of ratcheting teeth may extend in a radially outward direction away from the outer surface 26 of the handle body 16.

Referring to FIG. 5, the first ring-shaped port 36 may be formed by the distal portion $16_D$ of the handle body 16. The first ring-shaped port 36 may include an exterior side surface 42, an interior side surface 44 and a distal end surface 46 that connects the exterior side surface 42 to the interior side surface 44. The exterior side surface 42 and the distal end surface 46 are defined by the outer surface 26 of the handle body 16. The interior side surface 44 is defined by the inner surface 24 of the handle body 16. The interior side surface 44 defines the snare passage 30 that extends through the first ring-shaped port 36.

With continued reference to FIG. 5, the second ring-shaped port 38 may be formed by the intermediate portion $16_I$ of the handle body 16. The second ring-shaped port 38 may include an exterior side surface 48, an interior side surface 50 and a distal end surface 52 that connects the exterior side surface 48 to the interior side surface 50. The exterior side surface 48 and the distal end surface 52 are defined by the outer surface 26 of the handle body 16. The interior side surface 50 is defined by the inner surface 24 of the handle body 16. The interior side surface 50 defines the cautery device passage 32 that extends through the second ring-shaped port 38.

Figure 6:
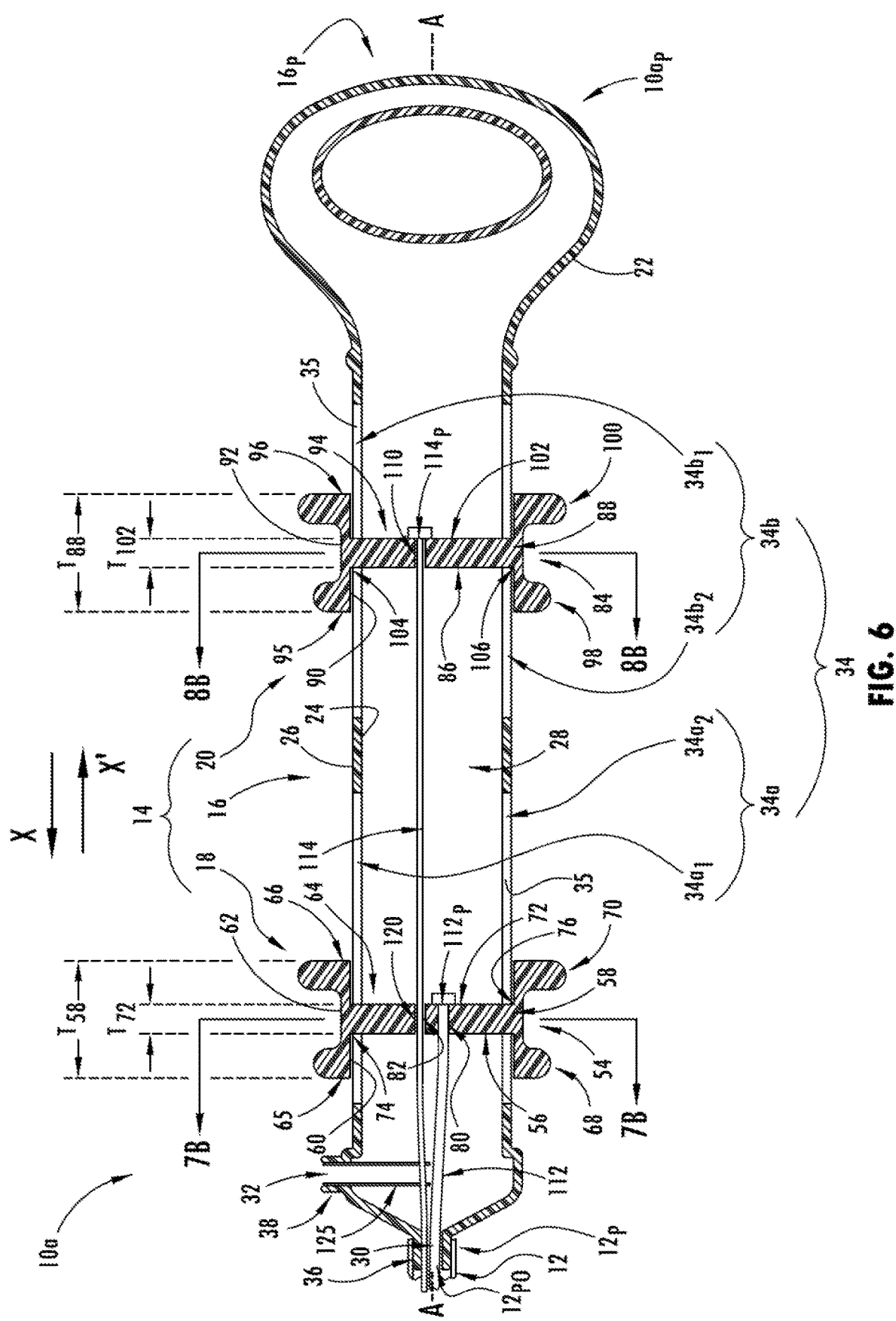
FIG. 6 is a cross-sectional view of the snare subassembly portion according to line 6-6 of FIG. 2.

Referring to FIG. 6, the first plunger 18 is movably-connected to the handle body 16. The first plunger 18 is axially-movable according to a first axial direction X or a second axial direction X' that is opposite the first axial direction X.

Figure 7:
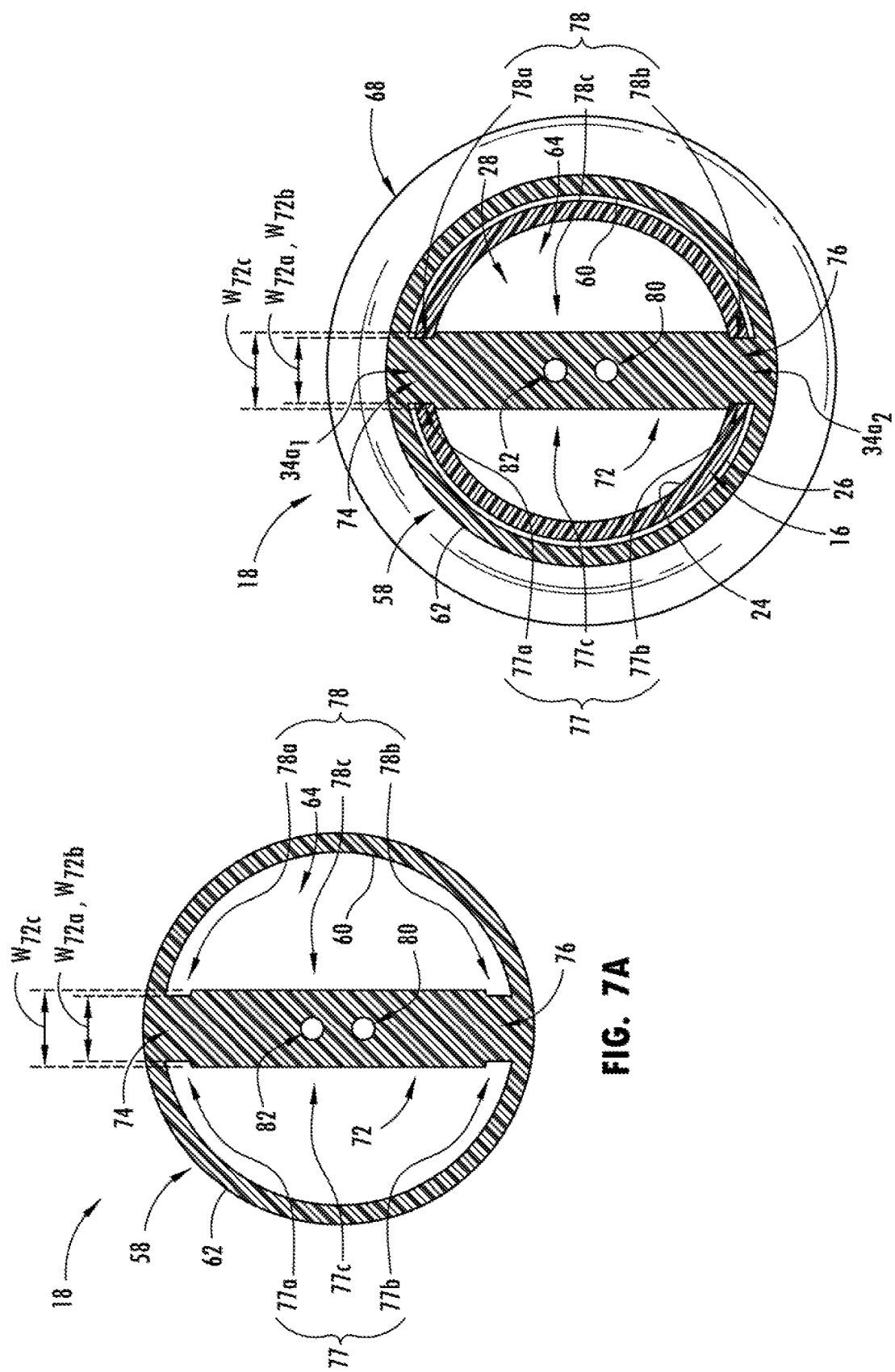
FIG. 7A is a cross-sectional view of a first plunger of the snare subassembly portion referenced from line 7B-7B of FIG. 6.
FIG. 7B is a cross-sectional view of the snare subassembly portion according to line 7B-7B of FIG. 6.

Referring to FIG. 6, the first plunger 18 includes an axial portion 54 and a radial portion 56. As seen in FIGS. 6 and 7A, the axial portion 54 may be defined by a ring-shaped body 58 having a thickness $T_{58}$ (see FIG. 6). The ring-shaped body 58 may be defined by an inner surface 60 and an outer surface 62. The inner surface 60 defines a passage 64 (see FIG. 7A) extending through the ring-shaped body 58. Referring to FIG. 6, the ring-shaped body 58 may include a distal end 65 and a proximal end 66. A first circumferential projection 68 may extend radially outwardly from the distal end 65 of the ring-shaped body 58. A second circumferential projection 70 may extend radially outwardly from the proximal end 66 of the ring-shaped body 58. The second circumferential projection 70 may extend radially outwardly at a distance greater than that of the first circumferential projection 68.

The radial portion 56 may be defined by a flange body 72 having a first end 74 and a second end 76. As seen in FIGS. 6 and 7B, the first end 74 of the flange body 72 extends through the first snare actuator passage $34a_1$ of the first snare actuator passage portion 34a, and, the second end 76 of the flange body 72 extends through the second snare actuator passage $34a_2$ of the first snare actuator passage portion 34a. By arranging the flange body 72 radially through the first snare actuator passage $34a_1$ and the second snare actuator passage $34a_2$ of the first snare actuator passage portion 34a, the first plunger 18 is permitted to axially slide X/X' relative the handle body 16; furthermore, because the flange body 72 radially extends through the through the first snare actuator passage $34a_1$ and the second snare actuator passage $34a_2$ of the first snare actuator passage portion 34a, the first plunger 18 is not permitted to rotate about the outer surface 26 of the handle body 16. In some instances, if the frictional surface 40 extends from the passage surface 35 of the handle body 16 as described above, side surface portions 77a, 77b, 78a, 78b of one or more of the first end 74 of the flange body 72 and the second end 76 of the flange body 72 may engage the frictional surface 40 as the first plunger 18 axially slides X/X' relative the handle body 16.

Referring to FIG. 10, a portion of the length of the handle body 16 that defines the first snare actuator passage portion 34a (for permitting the first plunger 18 to be movably-connected to the handle body 16 according to the direction of the arrows X/X') may also define the frictional surface 40. In some instances, the frictional surface 40 may extend along one or both of the first snare actuator passage $34a_1$ and the second snare actuator passage $34a_2$ of the first snare actuator passage portion 34a. In some examples, as seen, for example, in FIG. 2, the frictional surface 40 may be arranged between and extend along both of the first snare actuator passage $34a_1$ and the second snare actuator passage $34a_2$ of the first snare actuator passage portion 34a. In other examples, the frictional surface 40 may extend along one or both of the first snare actuator passage $34a_1$ and the second snare actuator passage $34a_2$ of the first snare actuator passage portion 34a at a distance that is less than, greater than or substantially the same as the first snare actuator passage $34a_1$ and the second snare actuator passage $34a_2$ of the first snare actuator passage portion 34a.

In some instances, as seen, for example, in FIGS. 2-3, if the frictional surface 40 may include a first frictional surface portion 40a and a second frictional surface portion 40b extending in diametrically opposing radially outward directions away from the outer surface 26 of the handle body 16. The first circumferential projection 68 extending radially outwardly from the distal end 65 of the ring-shaped body 58 of the axial portion 54 of the first plunger 18 may be radially separated, etched, scored or cut to form diametrically opposed ratchet release tabs $68_T$ (see, e.g., FIG. 2) that are respectively interfaced with the first frictional surface portion 40a and the second frictional surface portion 40b. As the first plunger 18 is axially moved X/X' relative the handle body 16, the ratchet release tabs $68_T$ may flex (and be subsequently locked or wedged about the first frictional surface portion 40a and the second frictional surface portion 40b) as the ratchet release tabs $68_T$ slide over the first frictional surface portion 40a and the second frictional surface portion 40b in order to axially selectively-fix the first plunger 18 relative the handle body 16. In the event the user wishes to adjust the axial orientation of the first plunger 18 relative the handle body 16, the user applies pressure to the ratchet release tabs $68_T$ for respectively flexing and releasing the ratchet release tabs $68_T$ from the first frictional surface portion 40a and the second frictional surface portion 40b such that the first plunger 18 is permitted to be axially selectively-adjusted relative the handle body 16.

As described above, the frictional surface 40 engages the first plunger 18 for impeding or selectively-preventing axial movement X/X' of the first plunger 18 relative the handle body 16. By impeding or selectively-preventing axial movement X/X' of the first plunger 18 relative the handle body 18, axial movement X/X' of the first snare shaft 112 relative the handle body 16 is impeded or selectively-prevented, which therefore impedes or selectively-prevents axial movement X/X' of the first snare loop 116 relative the handle body 16. By impeding or selectively-preventing axial movement X/X' of the first snare loop 116 relative the handle body 116, a user may selectively maintain a positioning of the first snare loop 116 against underlying colon tissue T (see, e.g., FIGS. 21A-21C) and around a polyp P (see, e.g., FIGS. 21A-21C) extending from the colon tissue T (although the presently described device may be utilized in the colon, the device may find alternative uses at other locations in the gastro-intestinal track, such as, for example: the small bowel, stomach or esophagus).

The flange body 72 extends across the passage 64 defined by the inner surface 60 of the ring-shaped body 58 such that the first end 74 of the flange body 72 and the second end 74 of the flange body 72 are connected to diametrically opposing portions of the inner surface 60 of the ring-shaped body 58. The flange body 72 may be defined by a thickness $T_{72}$ (see FIG. 6). The thickness $T_{72}$ of the flange body 72 may be less than the thickness $T_{58}$ of the ring-shaped body 58.

Referring to FIG. 7A, the flange body 72 may be defined by a first side surface 77 and a second side surface 78. The first side surface 77 may be defined by a first radial portion 77a, a second radial portion 77b and an intermediate radial portion 77c connecting the first radial portion 77a to the second radial portion 77b. The second side surface 78 may be defined by a first radial portion 78a, a second radial portion 78b and an intermediate radial portion 78c connecting the first radial portion 78a to the second radial portion 78b.

The first radial portion 77a of the first side surface 77 is arranged opposite the first radial portion 78a of the second side surface 78 thereby defining a first width $W_{72a}$ of the flange body 72. The second radial portion 77b of the first side surface 77 is arranged opposite the second radial portion 78b of the second side surface 78 thereby defining a second width $W_{72b}$ of the flange body 72. The intermediate radial portion 77c of the first side surface 77 is arranged opposite the intermediate radial portion 78c of the second side surface 78 thereby defining an intermediate width $W_{72c}$ of the flange body 72. The first width $W_{72a}$ of the flange body 72 may be approximately equal to the second width $W_{72b}$ of the flange body 72; the intermediate width $W_{72c}$ of the flange body 72 may be greater than both of the first width $W_{72a}$ of the flange body 72 and the second width $W_{72b}$ of the flange body 72.

Referring to FIGS. 6 and 7A, a first axial passage 80 may extend through the thickness $T_{72}$ of the flange body 72. A second axial passage 82 may extend through the thickness $T_{72}$ of the flange body 72. Each of the first axial passage 80 and the second axial passage 82 may be equally radially spaced from an axial center of the first plunger 18.

Referring to FIG. 6, the second plunger 20 is movably-connected to the handle body 16. The second plunger 20 is axially-movable according to the first axial direction X or the second axial direction X' that is opposite the first axial direction X.

Figure 8:
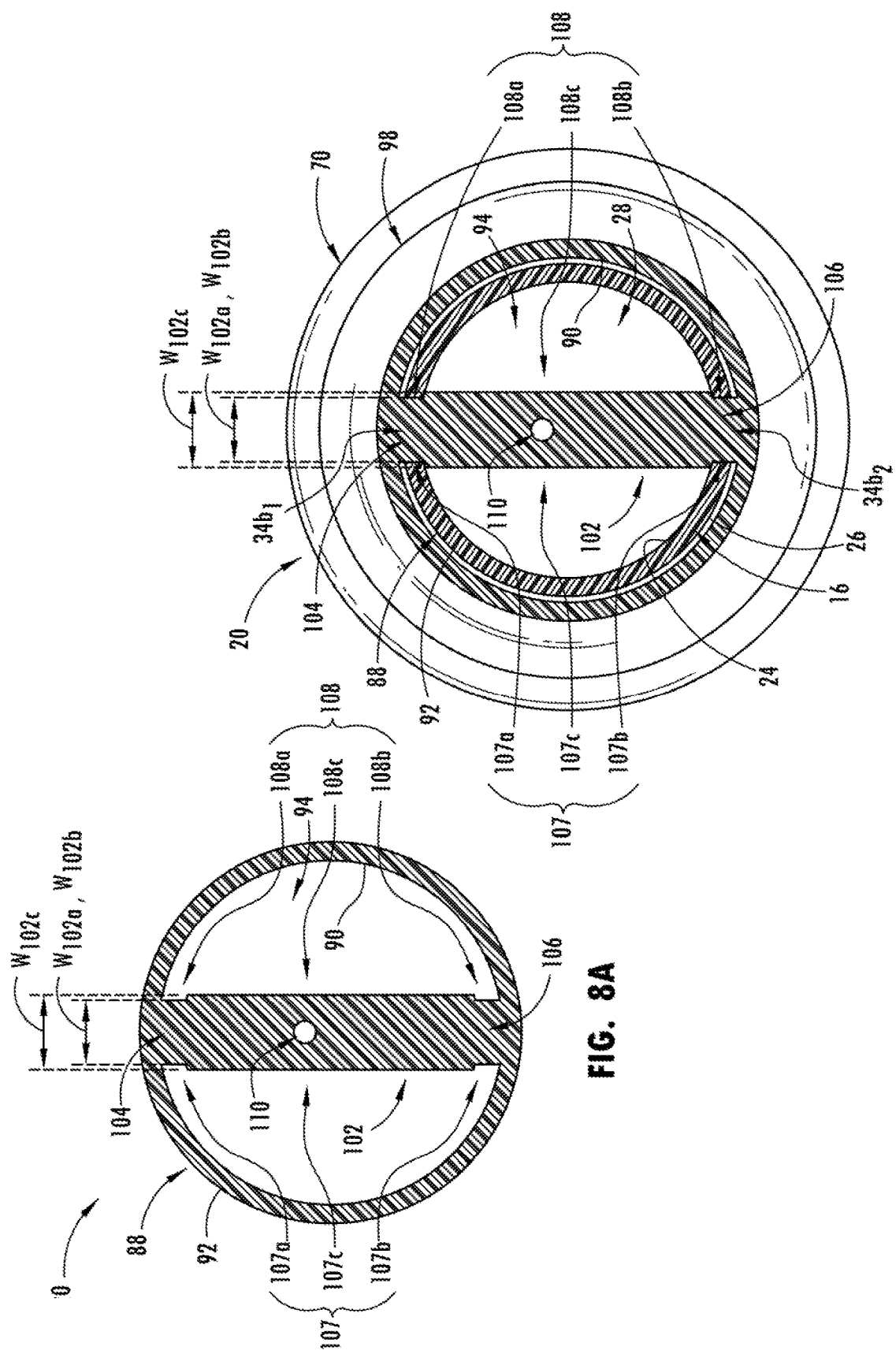
FIG. 8A is a cross-sectional view of a second plunger of the snare subassembly portion referenced from line 8B-8B of FIG. 6.
FIG. 8B is a cross-sectional view of the snare subassembly portion according to line 7B-7B of FIG. 6.

Referring to FIG. 6, the second plunger 20 includes an axial portion 84 and a radial portion 86. As seen in FIGS. 6 and 8A, the axial portion 84 may be defined by a ring-shaped body 88 having a thickness $T_{88}$ (see FIG. 6). The ring-shaped body 88 may be defined by an inner surface 90 and an outer surface 92. The inner surface 90 defines a passage 94 extending through the ring-shaped body 88. As seen in FIG. 6, the ring-shaped body 88 may include a distal end 95 and a proximal end 96. A first circumferential projection 98 may extend radially outwardly from the distal end 95 of the ring-shaped body 88. A second circumferential projection 100 may extend radially outwardly from the proximal end 96 of the ring-shaped body 88. The second circumferential projection 100 may extend radially outwardly at a distance greater than that of the first circumferential projection 98.

As seen in FIGS. 6 and 8A, the radial portion 86 may be defined by a flange body 102 having a first end 104 and a second end 106. As seen in FIGS. 6 and 8B, the first end 104 of the flange body 102 extends through the first snare actuator passage $34b_1$ of the second snare actuator passage portion 34b, and, the second end 106 of the flange body 102 extends through the second snare actuator passage $34b_2$ of the second snare actuator passage portion 34b. By arranging the flange body 102 radially through the first snare actuator passage $34b_1$ and the second snare actuator passage $34b_2$ of the second snare actuator passage portion 34b, the second plunger 20 is permitted to axially slide X/X' relative to the handle body 16; furthermore, because the flange body 102 radially extends through the through the first snare actuator passage $34b_1$ and the second snare actuator passage $34b_2$ of the second snare actuator passage portion 34b, the second plunger 20 is not permitted to rotate about the outer surface 26 of the handle body 16.

The flange body 102 extends across the passage 94 defined by the inner surface 90 of the ring-shaped body 88 such that the first end 104 of the flange body 102 and the second end 104 of the flange body 102 are connected to diametrically opposing portions of the inner surface 90 of the ring-shaped body 88. The flange body 102 may be defined by a thickness $T_{102}$ (see FIG. 6). The thickness $T_{102}$ of the flange body 102 may be less than the thickness $T_{88}$ of the ring-shaped body 88.

Referring to FIG. 8A, the flange body 102 may be defined by a first side surface 107 and a second side surface 108. The first side surface 107 may be defined by a first radial portion 107a, a second radial portion 107b and an intermediate radial portion 107c connecting the first radial portion 107a to the second radial portion 107b. The second side surface 108 may be defined by a first radial portion 108a, a second radial portion 108b and an intermediate radial portion 108c connecting the first radial portion 108a to the second radial portion 108b.

The first radial portion 107a of the first side surface 107 is arranged opposite the first radial portion 108a of the second side surface 108 thereby defining a first width $W_{102a}$ of the flange body 102. The second radial portion 107b of the first side surface 107 is arranged opposite the second radial portion 108b of the second side surface 108 thereby defining a second width $W_{102b}$ of the flange body 102. The intermediate radial portion 107c of the first side surface 107 is arranged opposite the intermediate radial portion 108c of the second side surface 108 thereby defining an intermediate width $W_{102c}$ of the flange body 102. The first width $W_{102a}$ of the flange body 102 may be approximately equal to the second width $W_{102b}$ of the flange body 102; the intermediate width $W_{102c}$ of the flange body 102 may be greater than both of the first width $W_{102a}$ of the flange body 102 and the second width $W_{102b}$ of the flange body 102.

An axial passage 110 may extend through the thickness $T_{102}$ of the flange body 102. The axial passage 110 may be radially spaced from an axial center of the second plunger 20.

Figure 9:
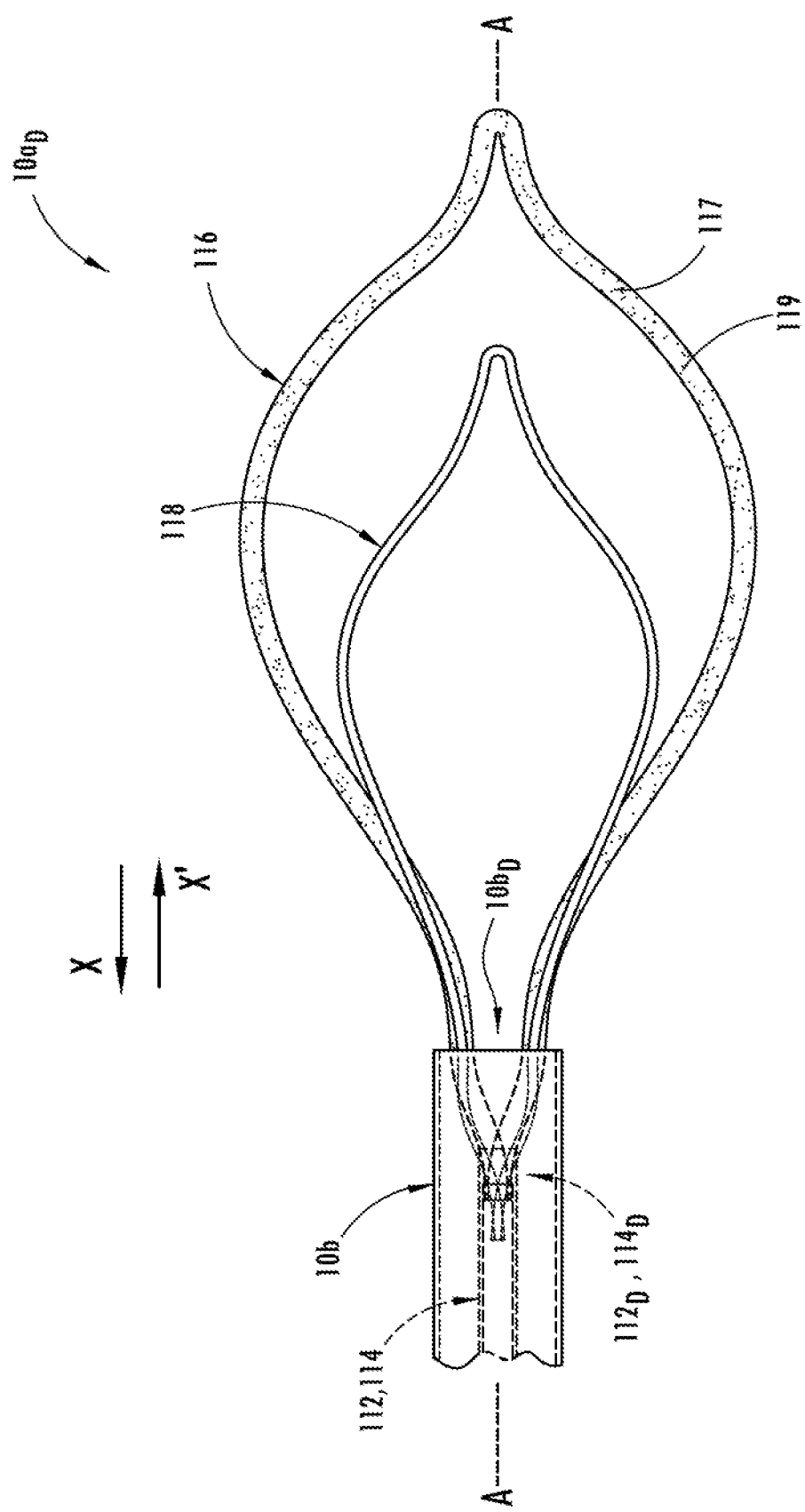
FIG. 9 is an enlarged view of a distal portion of the endoscopic catheter assembly according to line 9 of FIG. 1.

Referring to FIGS. 6 and 9, a first snare shaft 112 includes a proximal end $112_P$ (see, e.g., FIG. 6) and a distal end $112_D$ (see, e.g., FIG. 9). With continued reference to FIGS. 6 and 9, a second snare shaft 114 includes a proximal end $114_P$ (see, e.g., FIG. 6) and a distal end $114_D$ (see, e.g., FIG. 9).

As seen in FIG. 6, the proximal end 112P of the first snare shaft 112 is axially-fixedly-arranged within the first axial passage 80 extending through the thickness T72 of the flange body 72 of the first plunger 18 for connecting the proximal end 112P of the first snare shaft 112 to the first plunger 18. Referring to FIG. 9, the distal end 112D of the first snare shaft 112 is connected to a first snare loop 116. Furthermore, as seen in FIG. 9, an outer surface 117 of the first snare loop 116 may include a tissue-engaging, frictional surface 119, for example, an alimentary canal tissue, for example, esophagus, stomach, small intestine, colon and the like. The tissue-engaging, frictional surface 119 may include one or more of and/or a combination of: embossed portions, recesses, shapes (e.g., circular shapes, triangular shapes, sinusoidal shapes, arcuate shapes), slits, cuts, siping or the like.

The first snare loop 116, or, alternatively, both of the first snare shaft 112 and the first snare loop 116 may be derived from a surgical-grade non-conductive material (although, in some instances, surgical-grade conductive materials may alternatively be utilized). Non-limiting examples of a suitable non-conductive material may include plastic (e.g., vinyl, polypropylene, polyethylene), silicon or the like.

As seen in FIG. 6, the proximal end $114_P$ of the second snare shaft 114 is axially-fixedly-arranged within the axial passage 110 extending through the thickness $T_{102}$ of the flange body 102 of the second plunger 20 for connecting the proximal end $114_P$ of the second snare shaft 114 to the second plunger 20. Referring to FIG. 9, the distal end $114_D$ of the second snare shaft 114 is connected to a second snare loop 118. Furthermore, as seen in FIG. 6, an intermediate portion of a length 120 of the second snare shaft 114 axially extends through the second axial passage 82 extending through the thickness $T_{72}$ of the flange body 72 of the first plunger 18 in order to permit the second snare shaft 114 to be axially displaceable relative to the first plunger 18.

The second snare loop 118, or, alternatively, both of the second snare shaft 114 and the second snare loop 118 may be derived from a surgical-grade conductive material that may be subjected to, for example, a monopolar current or a bipolar current. Non-limiting examples of a suitable conductive material may include braided stainless steel wire, Nitinol, tungsten or the like. In some instances, the diameter of one or both of the material defining the second snare shaft 114 and the second snare loop 118 may range between approximately about 0.30 mm and 0.47 mm.

Referring to FIGS. 9, 11A-11C and 12A-12C, the first snare loop 116 may include a tear-drop shape. Similarly, as seen in FIGS. 9, 11A-11C and 12A-12C, the second snare loop 118 may include a tear-drop shape.

As described above, both of the first plunger 18 and the second plunger 20 are axially displaceable relative to the handle body 16 according to the first axial direction X or the second axial direction X' that is opposite the first axial direction X. When a user imparts axial movement X/X' to the first plunger 18, corresponding axial movement X/X' is imparted to the first snare shaft 112, which also imparts corresponding axial movement X/X' to the first snare loop 116. Similarly, when a user imparts axial movement X/X' to the second plunger 20, corresponding axial movement X/X' is imparted to the second snare shaft 114, which also imparts corresponding axial movement X/X' to the second snare loop 118.

When axial movement is applied to the first plunger 18 according to the direction of the arrow X toward the distal portion 16D of the handle body 16, the first snare shaft 112 is urged for axial displacement from a location within the interior cavity 28 of the handle body 16 and through: (1) the snare passage 30 extending axially through the handle body 16, (2) a proximal opening $12_{PO}$ (see, e.g., FIG. 6) formed by the proximal portion $10b_P$ of the catheter portion 10b, (3) a passage 12 formed by the catheter portion 10b, and (4) a distal opening $12_{DO}$ (see, e.g., FIGS. 11A-11C, 12A-12C) formed by the distal portion $10b_D$ of the catheter portion 10b such that the first snare loop 116 may be arranged exterior of the catheter portion 10b proximate the distal opening $12_{DO}$ formed by the distal portion $10b_D$ of the catheter portion 10b. Similarly, when axial movement is applied to the second plunger 20 according to the direction of the arrow X toward the distal portion 16D of the handle body 16, the second snare shaft 114 is urged for axial displacement from a location within the interior cavity 28 of the handle body 16 and through: (1) the snare passage 30 extending axially through the handle body 16, (2) the proximal opening $12_{PO}$ formed by the proximal portion $10b_P$ of the catheter portion 10b, (3) the passage 12 formed by the catheter portion 10b, and (4) the distal opening $12_{DO}$ formed by the distal portion $10b_D$ of the catheter portion 10b such that the second snare loop 118 may be arranged exterior of the catheter portion 10b proximate the distal opening $12_{DO}$ formed by the distal portion $10b_D$ of the catheter portion 10b.

Conversely, when axial movement is applied to the first plunger 18 according to the direction of the arrow X' toward the proximal portion 16p of the handle body 16, the first snare shaft 112 is urged for axial displacement from a location that permits arrangement of the first snare loop 116 exterior of the catheter portion 10b proximate the distal opening $12_{DO}$ formed by the distal portion $10b_D$ of the catheter portion 10b and through: (1) the distal opening $12_{DO}$ formed by the distal portion $10b_D$ of the catheter portion 10b, (2) the passage 12 formed by the catheter portion 10b, and (3) the proximal opening $12_{PO}$ formed by the proximal portion $10b_P$ of the catheter portion 10b. Similarly, when axial movement is applied to the second plunger 20 according to the direction of the arrow X' toward the proximal portion $16_P$ of the handle body 16, the second snare shaft 114 is urged for axial displacement from a location that permits arrangement of the second snare loop 118 exterior of the catheter portion 10b proximate the distal opening $12_{DO}$ formed by the distal portion $10b_D$ of the catheter portion 10b and through: (1) the distal opening $12_{DO}$ formed by the distal portion $10b_D$ of the catheter portion 10b, (2) the passage 12 formed by the catheter portion 10b, and (3) the proximal opening $12_{PO}$ formed by the proximal portion $10b_P$ of the catheter portion 10b.

Prior to imparting axial movement of the first snare shaft 112/the second snare shaft 114 according to the direction of arrow X, the first snare loop 116/the second snare loop 118 may be arranged within the passage 12 of the catheter portion 10b in a stowed orientation (see, e.g., step 210 in FIG. 19), proximate the distal opening $12_{DO}$ formed by the distal portion $10b_D$ of the catheter portion 10b; when arranged within the passage 12 of the catheter portion 10b, the first snare loop 116/the second snare loop 118 is/are arranged in a retracted and collapsed orientation. However, when axial movement of the first snare shaft 112/the second snare shaft 114 occurs according to the direction of arrow X (see, e.g., step 216 in FIG. 19) such that the first snare loop 116/the second snare loop 118 is/are arranged exterior of the catheter portion 10b proximate the distal opening $12_{DO}$ formed by the distal portion $10b_D$ of the catheter portion 10b, the first snare loop 116/the second snare loop 118 is/are permitted to transition from the retracted and collapsed orientation to a deployed and expanded orientation.

Conversely, prior to imparting axial movement of the first snare shaft 112/the second snare shaft 114 according to the direction of arrow X', the first snare loop 116/the second snare loop 118 may be arranged exterior of the catheter portion 10b proximate the distal opening $12_{DO}$ formed by the distal portion $10b_D$ of the catheter portion 10b; when arranged exterior of the passage 12 of the catheter portion 10b, the first snare loop 116/the second snare loop 118 is/are arranged in the deployed and expanded orientation. However, when axial movement of the first snare shaft 112/the second snare shaft 114 occurs according to the direction of arrow X' such that the first snare loop 116/the second snare loop 118 is/are arranged within the passage 12 of the catheter portion 10b proximate the distal opening $12_{DO}$ formed by the distal portion $10b_D$ of the catheter portion 10b, the first snare loop 116/the second snare loop 118 is/are permitted to transition from the deployed and expanded orientation to the retracted and collapsed orientation.

Figure 11C:
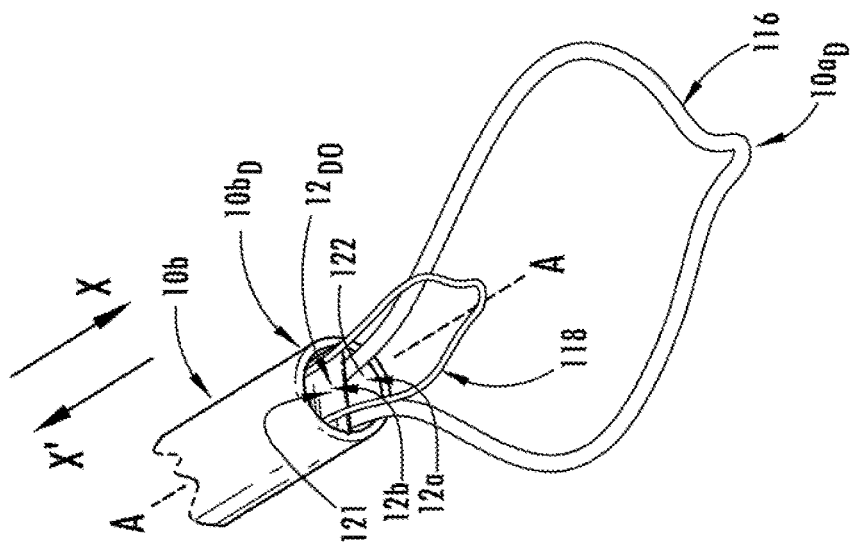
FIGS. 11A-11C are perspective views of a distal portion of an exemplary snare subassembly portion and a distal portion of an exemplary catheter portion of an exemplary endoscopic catheter assembly.
Figure 11B:
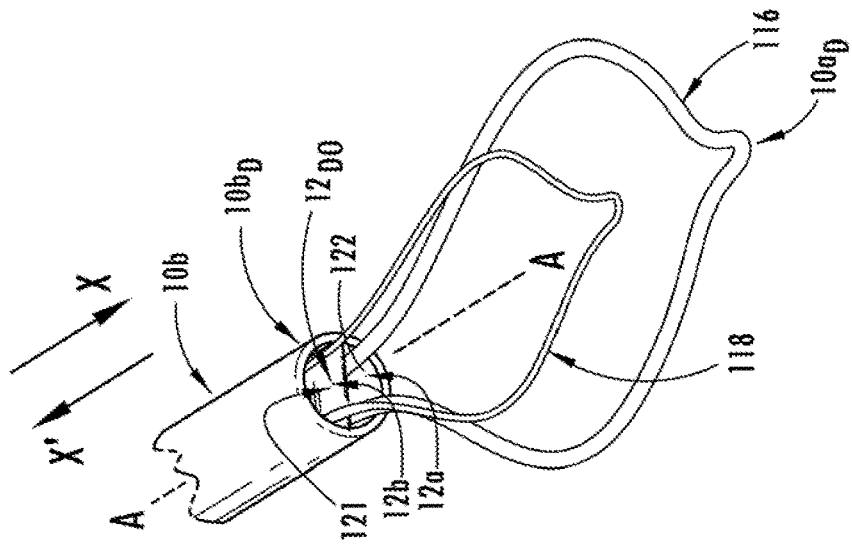
Figure 11A:
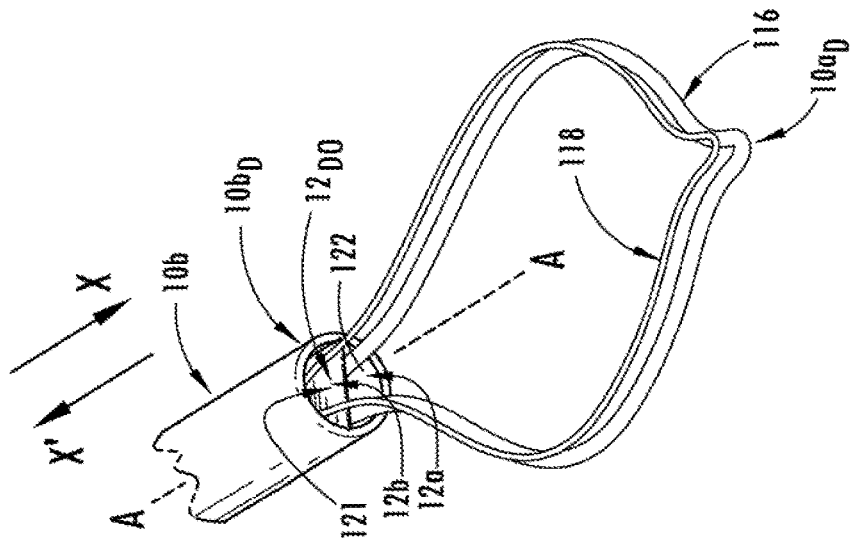

Referring to FIGS. 11A-11C, in an example, the passage 12 formed by the catheter portion 10b may be bifurcated to define a first passage portion 12a and a second passage portion 12b by extending a radial wall 121 across diametrically-opposing portions of the inner surface 122 of the passage 12. The radial wall 121 divides at least a portion of the length of the passage 12 proximate the distal opening $12_{DO}$ formed by the distal portion $10b_D$ of the catheter portion 10b into a first passage portion 12a and a second passage portion 12b. The first passage portion 12a may function by: (1) guiding a portion of the length of the first snare shaft 112 proximate the distal end $112_D$ of the first snare shaft 112, and (2) containing the first snare loop 116 when the first snare loop 116 is arranged in the collapsed orientation within the passage 12 as described above. The second passage portion 12b may function by: (1) guiding a portion of the length of the second snare shaft 114 proximate the distal end $114_D$ of the second snare shaft 114, and (2) containing the second snare loop 118 when the second snare loop 118 is arranged in the collapsed orientation within the passage 12 as described above.

Figure 12C:
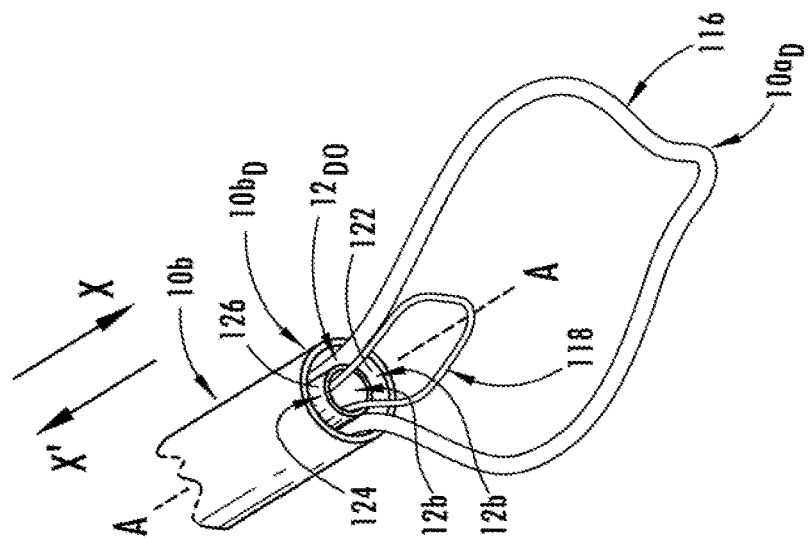
FIGS. 12A-12C are perspective views of a distal portion of an exemplary snare subassembly portion and a distal portion of an exemplary catheter portion of an exemplary endoscopic catheter assembly.
Figure 12B:
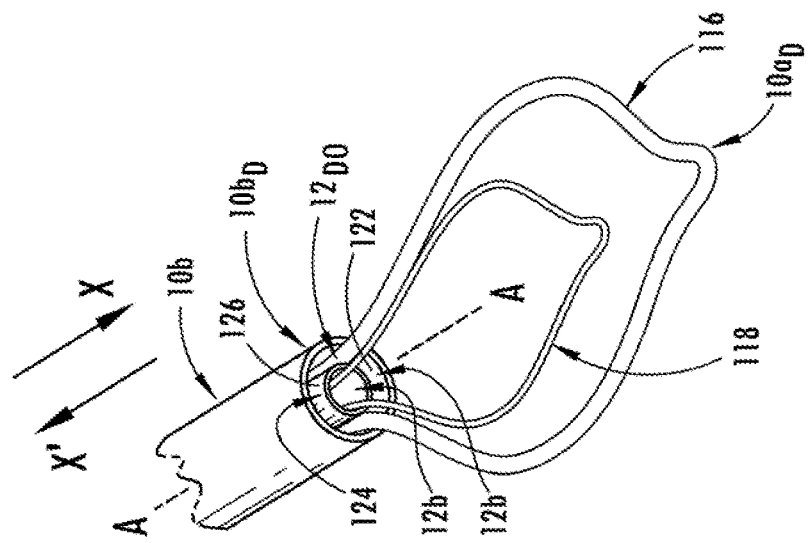
Figure 12A:
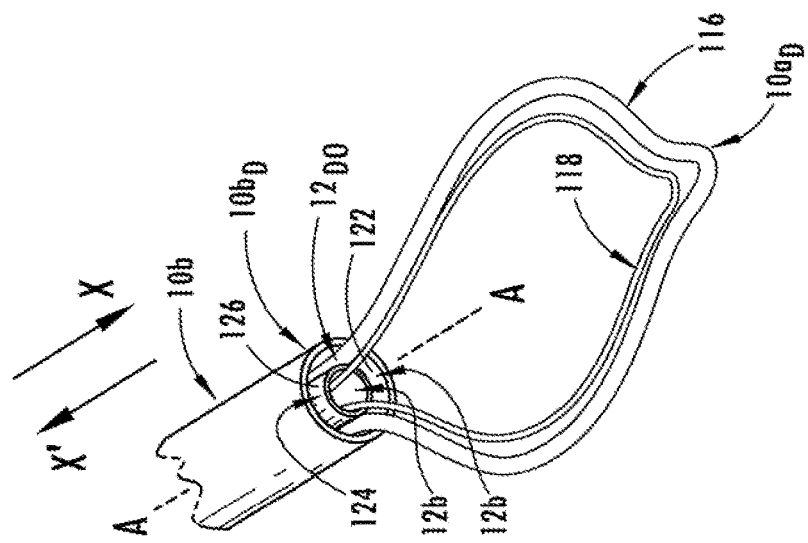

Referring to FIGS. 12A-12C, in an example, the passage 12 formed by the catheter portion 10b may be bifurcated to define a first passage portion 12a and a second passage portion 12b by arranging a tube-shaped member 124 within the passage 12. The tube-shaped member 124 may be arranged in a radially spaced apart relationship with respect to the inner surface 122 of the passage by, for example, one or more radially-projecting ribs (not shown) that connects an outer surface 126 of the tube-shaped member 124 to the inner surface 122 of the passage 12. The tube-shaped member 124 divides at least a portion of the length of the passage 12 proximate the distal opening $12_{DO}$ formed by the distal portion $10b_D$ of the catheter portion 10b into a first passage portion 12a and a second passage portion 12b. The first passage portion 12a may function by: (1) guiding a portion of the length of the first snare shaft 112 proximate the distal end $112_D$ of the first snare shaft 112, and (2) containing the first snare loop 116 when the first snare loop 116 is arranged in the collapsed orientation within the passage 12 as described above. The second passage portion 12b may function by: (1) guiding a portion of the length of the second snare shaft 114 proximate the distal end $114_D$ of the second snare shaft 114, and (2) containing the second snare loop 118 when the second snare loop 118 is arranged in the collapsed orientation within the passage 12 as described above.

Referring to FIGS. 13A-13D, in an example, the passage 12 formed by the catheter portion 10b may be bifurcated to define a first passage portion 12a and a second passage portion 12b by arranging a tube-shaped member 124 within the passage 12. Unlike the exemplary embodiment described above at FIGS. 12A-12C, the tube-shaped member 124 is not arranged in a radially spaced apart relationship with respect to the inner surface 122 defining the passage by, for example, one or more radially-projecting ribs (not shown) that connects an outer surface 126 of the tube-shaped member 124 to the inner surface 122 defining the passage 12; rather, as seen in FIG. 13D, a portion of the circumference defining the outer surface 126 of the tube-shaped member 124 is joined directly to and extends from the inner surface 122 defining the passage. The tube-shaped member 124 divides at least a portion of the length of the passage 12 proximate the distal opening $12_{DO}$ formed by the distal portion $10b_D$ of the catheter portion 10b into the first passage portion 12a and the second passage portion 12b. The first passage portion 12a may function by: (1) guiding a portion of the length of the first snare shaft 112 proximate the distal end $112_D$ of the first snare shaft 112, and (2) containing the first snare loop 116 when the first snare loop 116 is arranged in the collapsed orientation within the passage 12 as described above. The second passage portion 12b may function by: (1) guiding a portion of the length of the second snare shaft 114 proximate the distal end $114_D$ of the second snare shaft 114, and (2) containing the second snare loop 118 when the second snare loop 118 is arranged in the collapsed orientation within the passage 12 as described above. Furthermore, unlike the exemplary embodiment described above at FIGS. 12A-12C, the tube-shaped member 124 seen at FIGS. 13A-13D is not concentrically arranged within the passage defined by the inner surface 122; rather, as seen in FIG. 13D, an axial center $A_{124}$ of the tube-shaped member 124 is radially offset from the central axis, A-A, extending through the axial center of the catheter portion 10b.

Figure 14A:
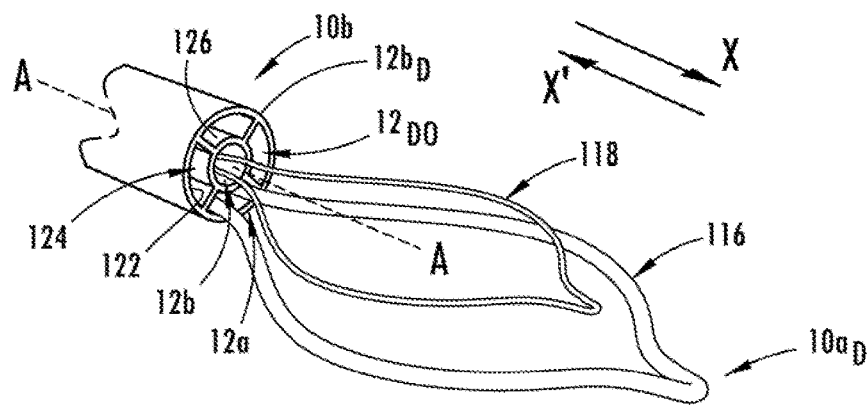
FIGS. 14A-14C are perspective views of a distal portion of an exemplary snare subassembly portion and a distal portion of an exemplary catheter portion of an exemplary endoscopic catheter assembly.
Figure 14B:
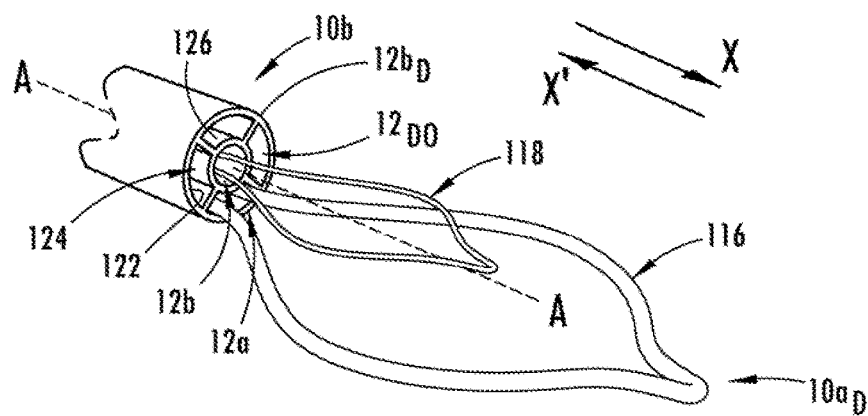
Figure 14C:
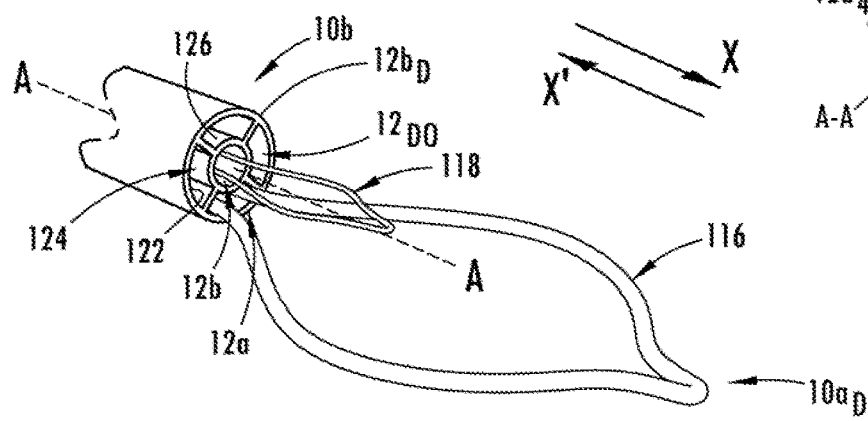
Figure 14D:
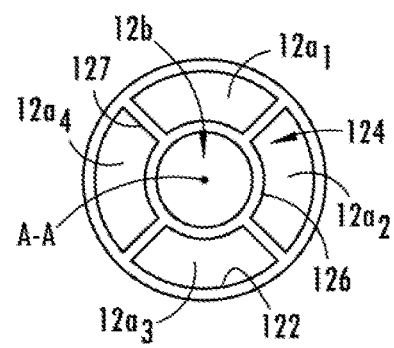
FIG. 14D is an end view of the distal portion of the exemplary snare subassembly portion and the distal portion of the exemplary catheter portion of the exemplary endoscopic catheter assembly of FIGS. 14A-14C.

Referring to FIGS. 14A-14D, in an example, the passage 12 formed by the catheter portion 10b may define a first passage portion 12a and a second passage portion 12b by arranging a tube-shaped member 124 within the passage 12. The tube-shaped member 124 may be arranged in a radially spaced apart relationship with respect to the inner surface 122 of the passage by, for example, four radially-projecting ribs 127 (see, e.g., FIG. 14D) that connects an outer surface 126 of the tube-shaped member 124 to the inner surface 122 of the passage 12. With reference to FIG. 14D, the tube-shaped member 124 divides at least a portion of the length of the passage 12 proximate the distal opening $12_{DO}$ formed by the distal portion $10b_D$ of the catheter portion 10b into the first passage portion 12a and the second passage portion 12b; the four radially-projecting ribs 127 divides at least a portion of the length of the passage 12 proximate the distal opening $12_{DO}$ formed by the distal portion $10b_D$ of the catheter portion 10b into four first passage portions $12a_1$, $12a_2$, $12a_3$, $12a_4$. One of the first passage portions $12a_1$, $12a_2$, $12a_3$, $12a_4$ of the first passage portion 12a may function by: (1) guiding a portion of the length of the first snare shaft 112 proximate the distal end $112_D$ of the first snare shaft 112, and (2) containing the first snare loop 116 when the first snare loop 116 is arranged in the collapsed orientation within the passage 12 as described above. The second passage portion 12b may function by: (1) guiding a portion of the length of the second snare shaft 114 proximate the distal end $114_D$ of the second snare shaft 114, and (2) containing the second snare loop 118 when the second snare loop 118 is arranged in the collapsed orientation within the passage 12 as described above.

Figure 15A:
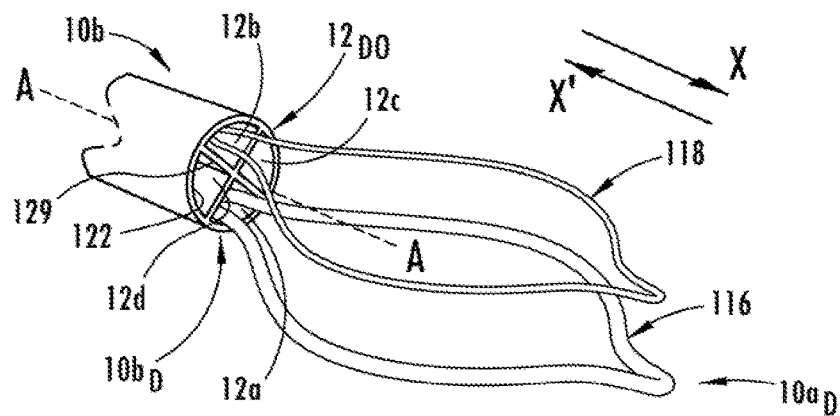
FIGS. 15A-15C are perspective views of a distal portion of an exemplary snare subassembly portion and a distal portion of an exemplary catheter portion of an exemplary endoscopic catheter assembly.
Figure 15B:
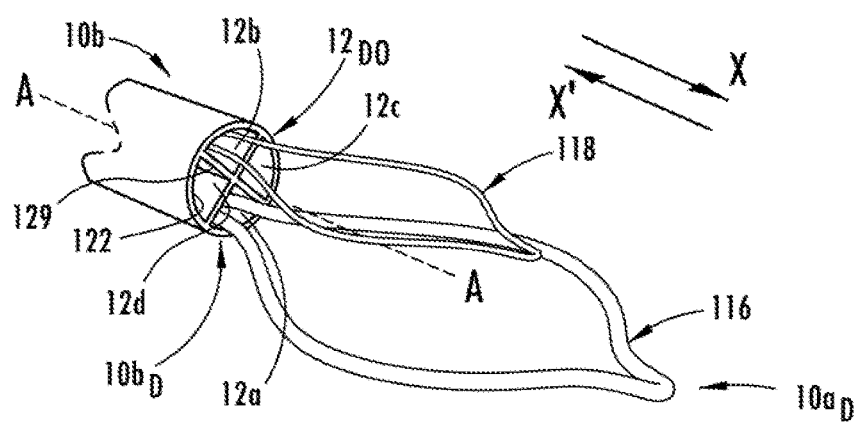
Figure 15C:
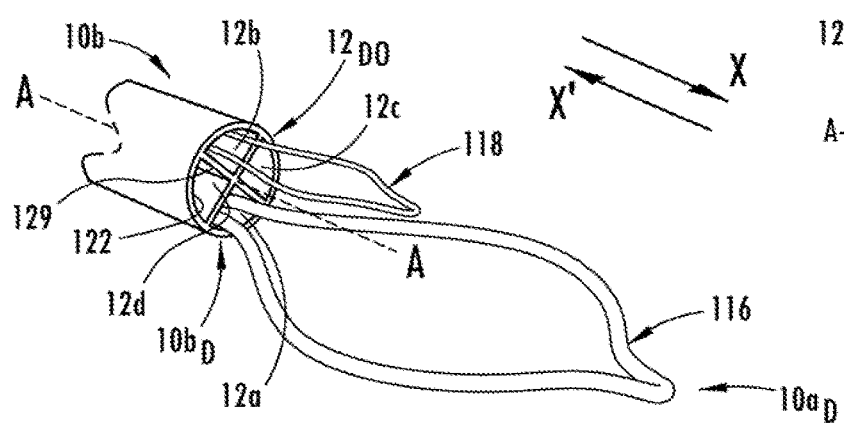
Figure 15D:
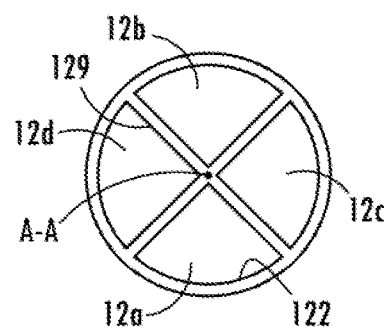
FIG. 15D is an end view of the distal portion of the exemplary snare subassembly portion and the distal portion of the exemplary catheter portion of the exemplary endoscopic catheter assembly of FIGS. 15A-15C.

Referring to FIGS. 15A-15D, in an example, the passage 12 formed by the catheter portion 10b may define a first passage portion 12a, a second passage portion 12b, a third passage portion 12c and a fourth passage portion 12d by arranging four radially-projecting ribs 129 within the passage 12. Each radially-projecting rib 129 of the four radially-projecting ribs 129 have a proximal end that is connected to the inner surface 122 of the passage 12 and a distal end that terminates at an axial center of the passage 12 such that the distal end of each radially-projecting rib 129 is connected to one another at the axial center of the passage 12. With reference to FIG. 15D, the four radially-projecting ribs 129 divides at least a portion of the length of the passage 12 proximate the distal opening $12_{DO}$ formed by the distal portion $10b_D$ of the catheter portion 10b into the first passage portion 12a, the second passage portion 12b, the third passage portion 12c and the fourth passage portion 12d. The first passage portions 12a may function by: (1) guiding a portion of the length of the first snare shaft 112 proximate the distal end $112_D$ of the first snare shaft 112, and (2) containing the first snare loop 116 when the first snare loop 116 is arranged in the collapsed orientation within the passage 12 as described above. The second passage portion 12b may function by: (1) guiding a portion of the length of the second snare shaft 114 proximate the distal end $114_D$ of the second snare shaft 114, and (2) containing the second snare loop 118 when the second snare loop 118 is arranged in the collapsed orientation within the passage 12 as described above. The third passage portion 12c and the fourth passage portion 12d define structural voids in the passage 12.

Figure 16A:
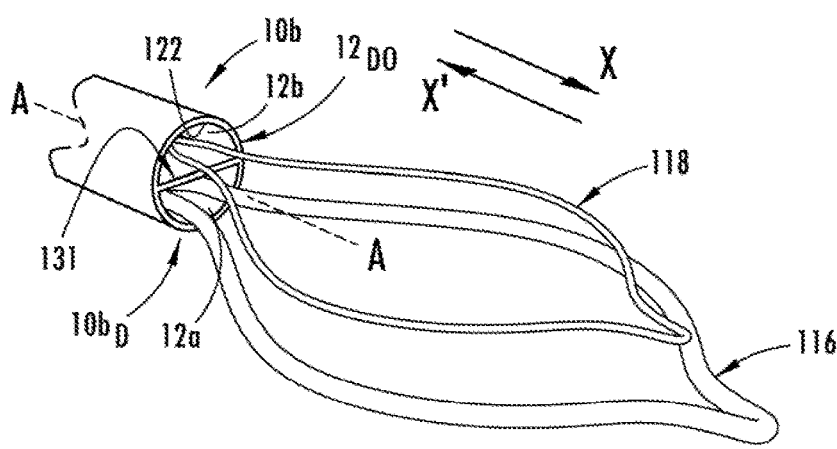
FIGS. 16A-16C are perspective views of a distal portion of an exemplary snare subassembly portion and a distal portion of an exemplary catheter portion of an exemplary endoscopic catheter assembly.
Figure 16B:
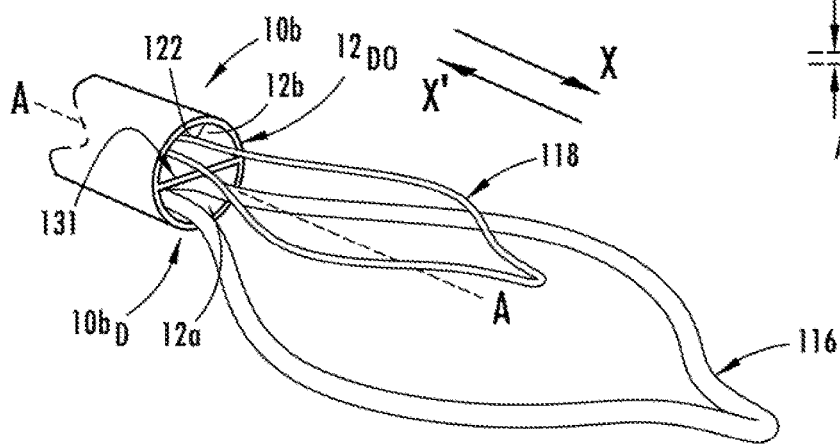
Figure 16C:
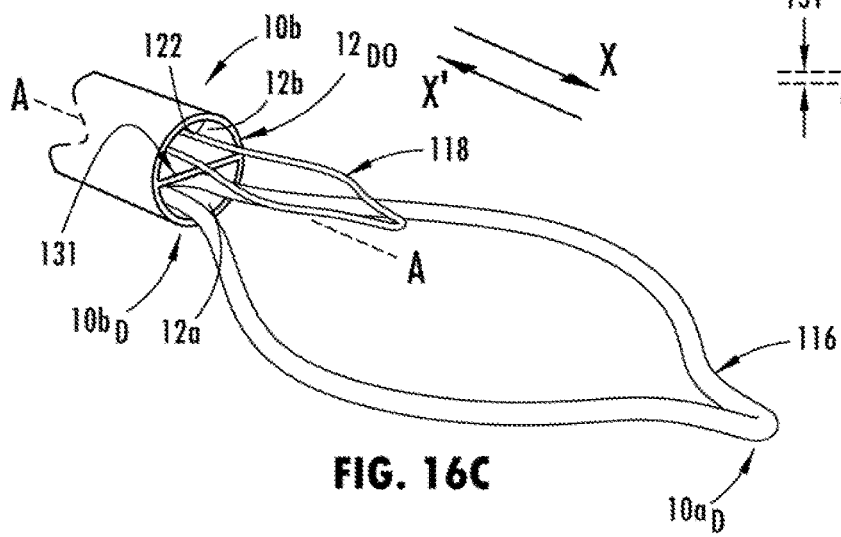
Figure 16D:
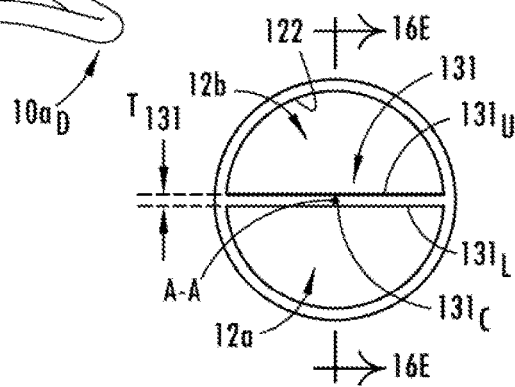
FIG. 16D is an end view of the distal portion of the exemplary snare subassembly portion and the distal portion of the exemplary catheter portion of the exemplary endoscopic catheter assembly of FIGS. 16A-16C.
Figure 16E:
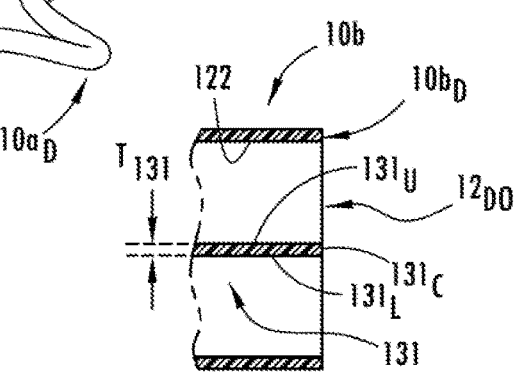
FIG. 16E is a cross-sectional view according to line 16E-16E of FIG. 16D.

Referring to FIGS. 16A-16E, in an example, the passage 12 formed by the catheter portion 10b may be bifurcated to define a first passage portion 12a and a second passage portion 12b by extending a radial blade portion 131 across diametrically-opposing portions of the inner surface 122 of the passage 12. The radial blade portion 131 divides at least a portion of the length of the passage 12 proximate the distal opening $12_{DO}$ formed by the distal portion $10b_D$ of the catheter portion 10b into a first passage portion 12a and a second passage portion 12b. The first passage portion 12a may function by: (1) guiding a portion of the length of the first snare shaft 112 proximate the distal end $112_D$ of the first snare shaft 112, and (2) containing the first snare loop 116 when the first snare loop 116 is arranged in the collapsed orientation within the passage 12 as described above. The second passage portion 12b may function by: (1) guiding a portion of the length of the second snare shaft 114 proximate the distal end $114_D$ of the second snare shaft 114, and (2) containing the second snare loop 118 when the second snare loop 118 is arranged in the collapsed orientation within the passage 12 as described above. Referring to FIGS. 16D-16E, the radial blade portion 131 may include a thickness $T_{131}$ extending between an upper surface $131_U$ and a lower surface $131_L$ of the radial blade portion 131. A cutting surface $131_C$ connects the upper surface $131_U$ to the lower surface $131_L$. As seen in FIG. 16E, the cutting surface $131_C$ extends substantially perpendicularly from each of the upper surface $131_U$ and the lower surface $131_L$; as a result, the cutting surface $131_C$ may be deemed to have a dull or blunt cutting surface profile. Furthermore, as also seen in FIG. 16E, the cutting surface $131_C$ may be substantially aligned with and not extend axially beyond the distal opening $12_{DO}$ formed by the distal portion $10b_D$ of the catheter portion 10b.

Figure 17A:
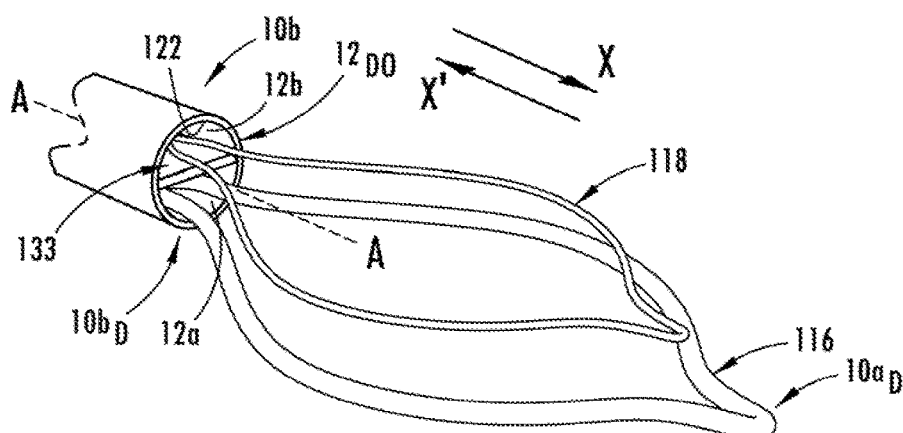
FIGS. 17A-17C are perspective views of a distal portion of an exemplary snare subassembly portion and a distal portion of an exemplary catheter portion of an exemplary endoscopic catheter assembly.
Figure 17B:
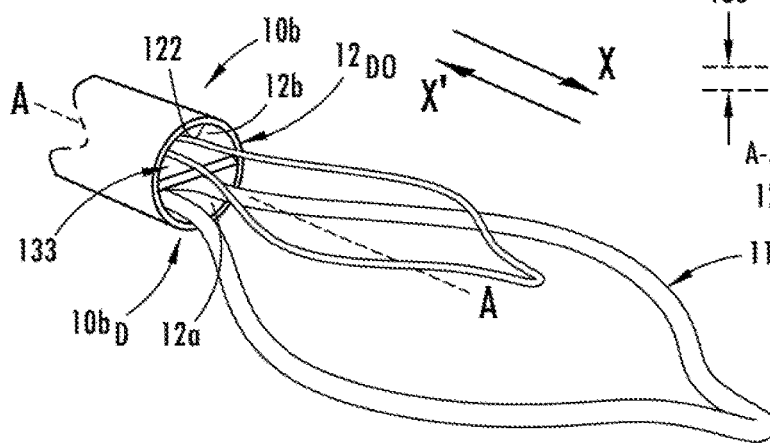
Figure 17C:
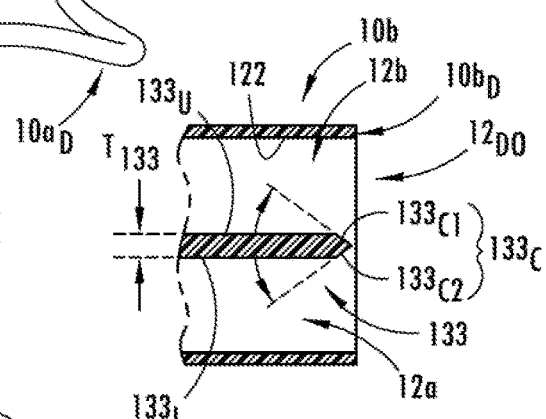
Figure 17D:
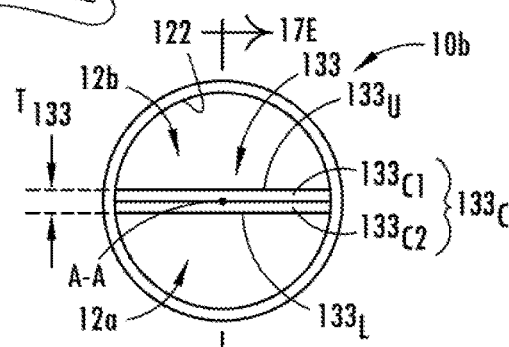
FIG. 17D is an end view of the distal portion of the exemplary snare subassembly portion and the distal portion of the exemplary catheter portion of the exemplary endoscopic catheter assembly of FIGS. 17A-17C.
Figure 17E:
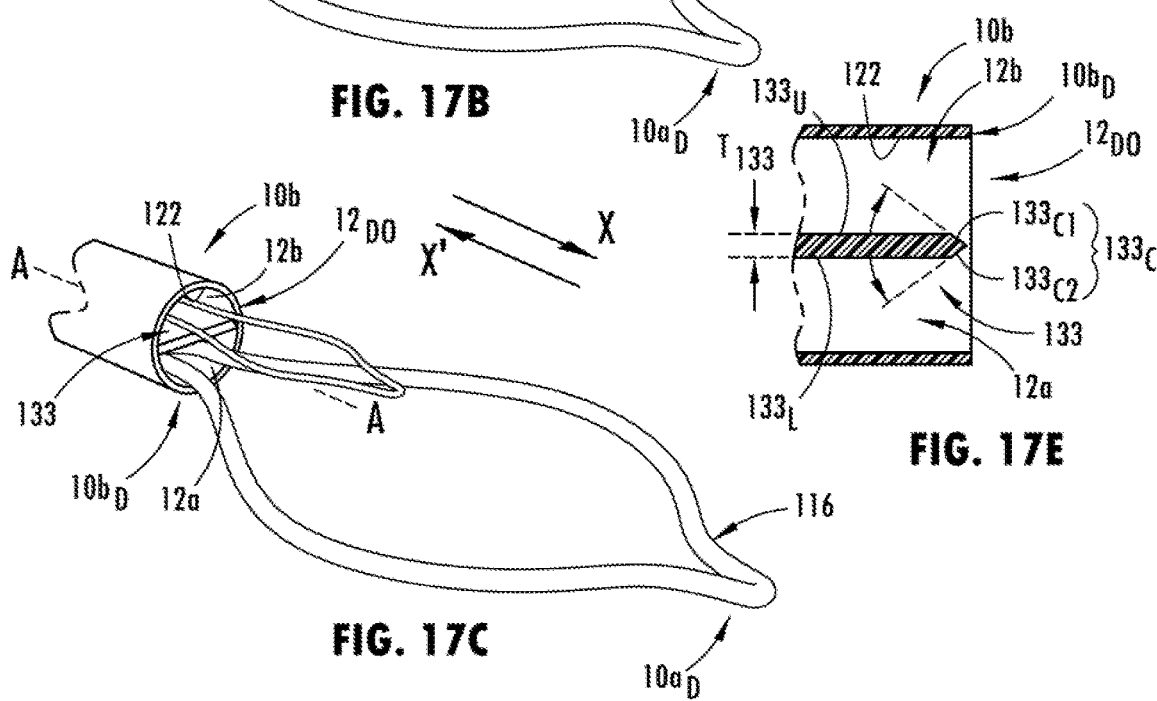
FIG. 17E is a cross-sectional view according to line 17E-17E of FIG. 17D.

Referring to FIGS. 17A-17E, in an example, the passage 12 formed by the catheter portion 10b may be bifurcated to define a first passage portion 12a and a second passage portion 12b by extending a radial blade portion 133 across diametrically-opposing portions of the inner surface 122 of the passage 12. The radial blade portion 133 divides at least a portion of the length of the passage 12 proximate the distal opening $12_{DO}$ formed by the distal portion $10b_D$ of the catheter portion 10b into a first passage portion 12a and a second passage portion 12b. The first passage portion 12a may function by: (1) guiding a portion of the length of the first snare shaft 112 proximate the distal end $112_D$ of the first snare shaft 112, and (2) containing the first snare loop 116 when the first snare loop 116 is arranged in the collapsed orientation within the passage 12 as described above. The second passage portion 12b may function by: (1) guiding a portion of the length of the second snare shaft 114 proximate the distal end 114$_D$ of the second snare shaft 114, and (2) containing the second snare loop 118 when the second snare loop 118 is arranged in the collapsed orientation within the passage 12 as described above. Referring to FIGS. 17D-17E, the radial blade portion 133 may include a thickness T$_{133}$ extending between an upper surface 133$_U$ and a lower surface 133$_L$ of the radial blade portion 133. A cutting surface 133$_C$ connects the upper surface 133$_U$ to the lower surface 133$_L$. As seen in FIG. 17E, the cutting surface 133$_C$ includes a first cutting surface portion 133$_{C1}$ that extends from the upper surface 133$_U$ and a second cutting surface portion 133$_{C2}$ that extends from the lower surface 133$_L$. The first cutting surface portion 133$_{C1}$ is connected to the second cutting surface portion 133$_{C2}$ to define a blade edge 133$_E$. The first cutting surface portion 133$_{C1}$ and the second cutting surface portion 133$_{C2}$ extend away from the blade edge 133$_E$ to define an angle θ resulting in a comparatively sharp cutting surface profile when compared to the dull or blunt cutting surface profile described above at FIG. 16E. Furthermore, as also seen in FIG. 17E, the blade edge 133$_E$ of the cutting surface 133$_{Cc}$ may be substantially aligned with and not extend axially beyond the distal opening 12$_{DO}$ formed by the distal portion 10b$_D$ of the catheter portion 10b.

Figure 18A:
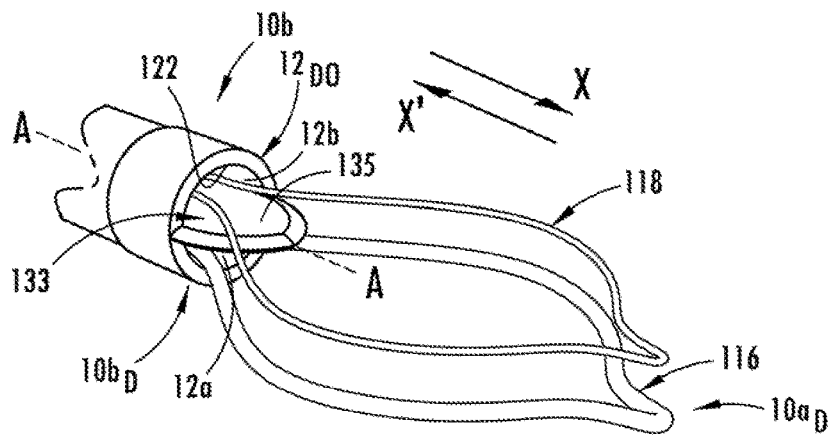
FIGS. 18A-18C are perspective views of a distal portion of an exemplary snare subassembly portion and a distal portion of an exemplary catheter portion of an exemplary endoscopic catheter assembly.
Figure 18B:
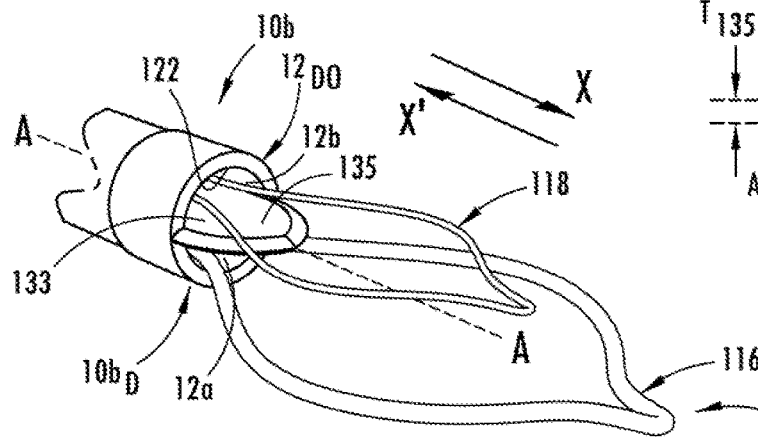
Figure 18D:
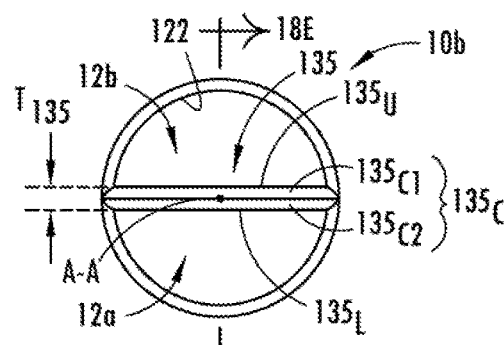
FIG. 18D is an end view of the distal portion of the exemplary snare subassembly portion and the distal portion of the exemplary catheter portion of the exemplary endoscopic catheter assembly of FIGS. 18A-18C.
Figure 18C:
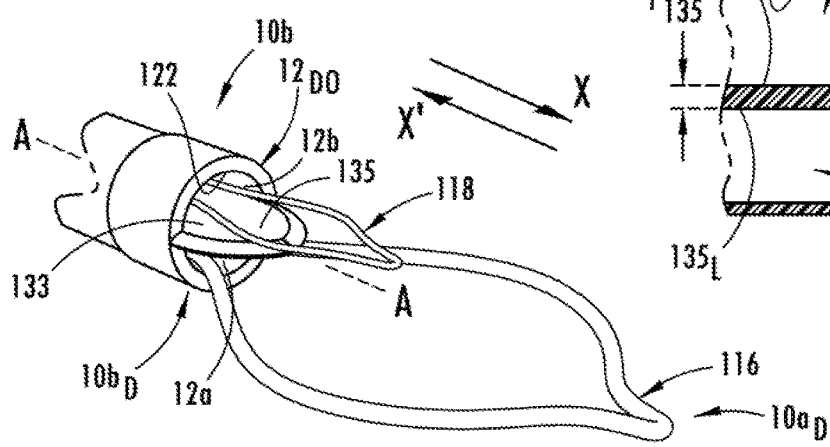
Figure 18E:
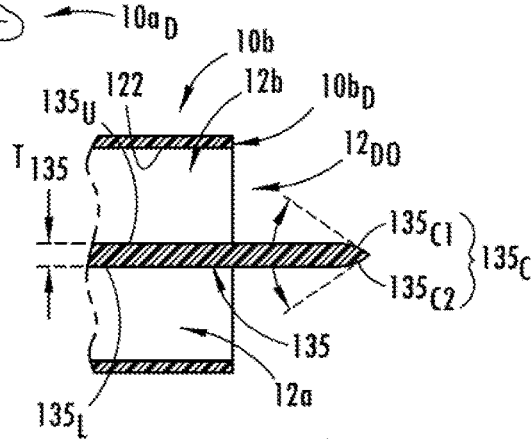
FIG. 18E is a cross-sectional view according to line 18E-18E of FIG. 18D.

Referring to FIGS. 18A-18E, in an example, the passage 12 formed by the catheter portion 10b may be bifurcated to define a first passage portion 12a and a second passage portion 12b by extending a radial blade portion 135 across diametrically-opposing portions of the inner surface 122 of the passage 12. The radial blade portion 135 divides at least a portion of the length of the passage 12 proximate the distal opening 12$_{DO}$ formed by the distal portion 10b$_D$ of the catheter portion 10b into a first passage portion 12a and a second passage portion 12b. The first passage portion 12a may function by: (1) guiding a portion of the length of the first snare shaft 112 proximate the distal end 112$_D$ of the first snare shaft 112, and (2) containing the first snare loop 116 when the first snare loop 116 is arranged in the collapsed orientation within the passage 12 as described above. The second passage portion 12b may function by: (1) guiding a portion of the length of the second snare shaft 114 proximate the distal end 114$_D$ of the second snare shaft 114, and (2) containing the second snare loop 118 when the second snare loop 118 is arranged in the collapsed orientation within the passage 12 as described above. Referring to FIGS. 18D-18E, the radial blade portion 135 may include a thickness T$_{135}$ extending between an upper surface 135$_U$ and a lower surface 135$_L$ of the radial blade portion 135. A cutting surface 135$_C$ connects the upper surface 135$_U$ to the lower surface 135$_L$. As seen in FIG. 18E, the cutting surface 135$_C$ includes a first cutting surface portion 135$_{C1}$ that extends from the upper surface 135$_U$ and a second cutting surface portion 135$_{C2}$ that extends from the lower surface 135$_L$. The first cutting surface portion 135$_{C1}$ is connected to the second cutting surface portion 135$_{C2}$ to define a blade edge 135$_E$. The first cutting surface portion 135$_{C1}$ and the second cutting surface portion 135$_{C2}$ extend away from the blade edge 135$_E$ to define an angle θ resulting in a comparatively sharp cutting surface profile when compared to the dull or blunt cutting surface profile described above at FIG. 16E. Unlike the embodiments described above at FIGS. 16E and 17E, as seen in FIG. 18E, the blade edge 135$_E$ of the cutting surface 135$_C$ extends axially beyond the distal opening 12$_{DO}$ formed by the distal portion 10b$_D$ of the catheter portion 10b.

Referring to FIG. 6, a plug member 125 may be optionally radially inserted into the second ring-shaped port 38 and through the cautery device passage 32. The plug member 125 may be further radially extended into the interior cavity 28 such that the plug member 125 may be connected to and interface with a portion of the length of the second snare shaft 114. As will be described in the following disclosure, the second snare shaft 114 permits the plug member 125 to be in communication with the second snare loop 118 to permit the second snare loop 118 to thermally separate a polyp P from the colon tissue T while cauterizing the colon tissue T.

Figure 19:
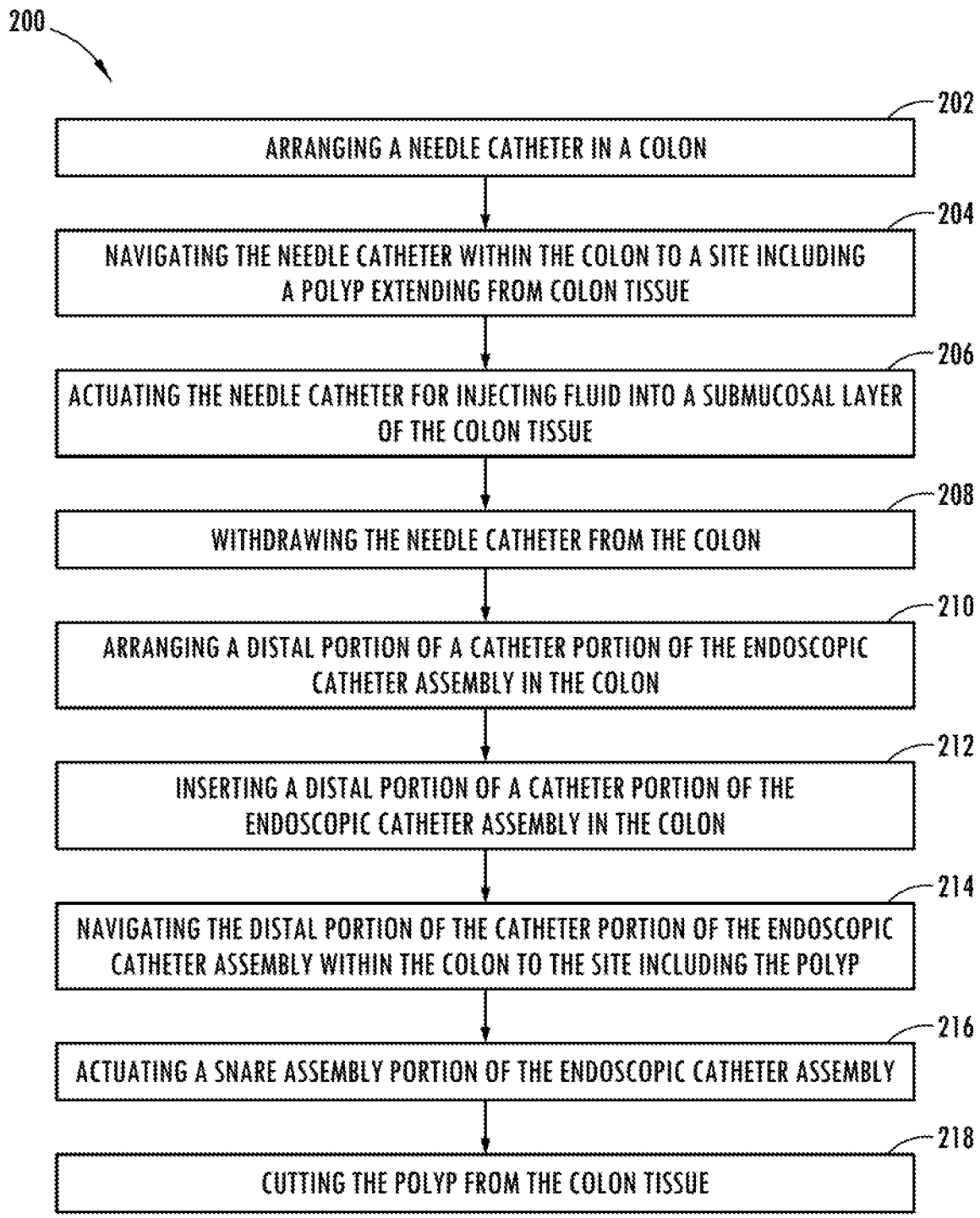
FIG. 19 is a flow diagram of a method for utilizing an endoscopic catheter assembly, which may be applied in the process of conducting a polypectomy procedure.

Referring to FIG. 19, a method is shown generally at 200. In various embodiments, the method disclosed in 200 is an exemplary method using a polypectomy method as an example of removing pathogenic tissue from surrounding healthy tissue using the devices of the present invention. As used herein, the term "pathogenic tissue" can also be referred to as diseased tissue. Pathogenic tissue may include tissue that is deemed by a medical professional as being worthy of removal during a surgical procedure. Without wishing to be bound by any scientific or medical theory, pathogenic tissue can include tissue that may cause further disease, make an existing disease worse or should be removed in view of sound medical judgment that is known to medical professionals practicing in the medical and surgical arts. In some examples, pathogenic tissue can include, but not limited to, a neoplasm, a cancer, a solid tumor, a metastatic cancer, a cancerous lesion, an inflamed tissue, a precancerous tissue, a necrotic tissue, an infected tissue, a calcified tissue, or combinations thereof. In various embodiments, removal of a pathogenic tissue, for example, a neoplasm, a cancer, a solid tumor, a metastatic cancer, a cancerous lesion, an inflamed tissue, a precancerous tissue, a necrotic tissue, an infected tissue, a calcified tissue, or combinations thereof can be achieved in any part of the subject's body, for example, removal of a cancer or solid tumor located in the subject's esophagus. In another example, the pathogenic tissue can include an infected cyst located in a subject's limb, surrounded by the subject's healthy muscle, fat, connective tissue, or subcutaneous tissue using the devices disclosed in the present invention. In another exemplary method, metastatic cancer lesions can be removed from the surrounding healthy lung tissue using the devices disclosed in the present invention. In some embodiments, the method 200 may include steps (see, e.g., steps 210-216) for operating the endoscopic catheter assembly 10. Additionally, the method 200 may alternatively be directed to a polypectomy procedure (see, e.g., steps 202-218) that includes the steps 210-216 for operating the endoscopic catheter assembly 10.

Figure 21A:
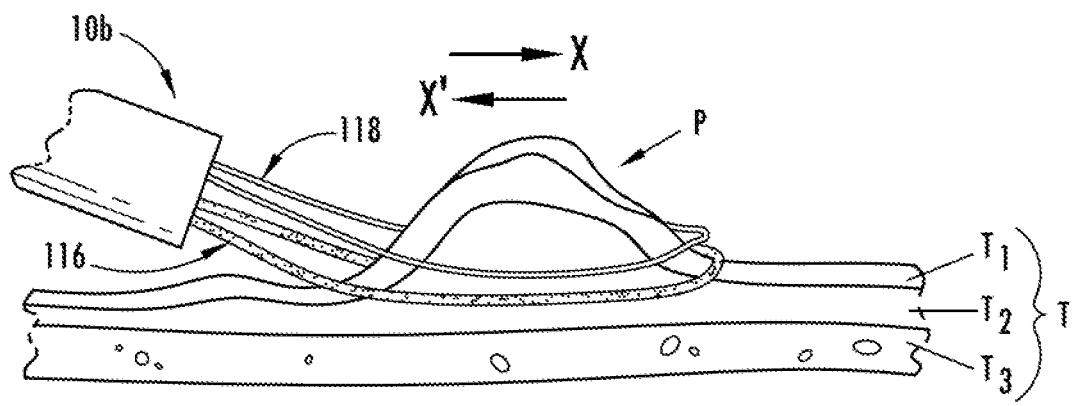
FIGS. 21A-21C are views of a distal portion of an exemplary snare subassembly portion and a distal portion of an exemplary catheter portion of an exemplary endoscopic catheter assembly conducting a polypectomy procedure.
Figure 21B:
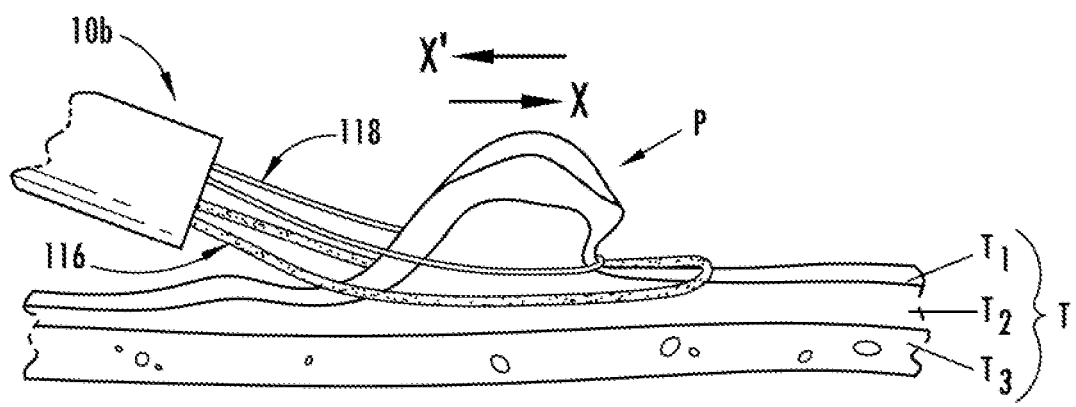
Figure 21C:
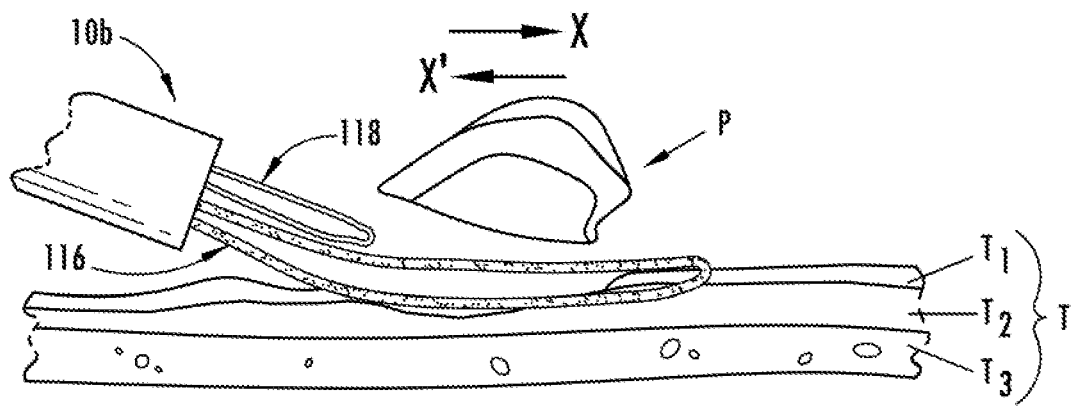

The polypectomy procedure may be initiated by inserting 202 a needle catheter (not shown) into the patient's colon C by an administrator (e.g., a doctor). The administrator may then navigate 204 the needle catheter within the colon C to the site of a polyp P extending from the colon tissue T. As seen in FIGS. 21A-21C, the colon tissue T may be defined by several layers of tissue (e.g., a mucosa layer T1, a submucosa layer T2 and a muscularis propria layer T3).

Once the needle catheter has been navigated 204 to the site of the polyp P, the administrator may actuate 206 the needle catheter for the purpose of injecting a fluid into a submucosal layer T$_2$ in a location proximate or below the polyp P. In response to the injection of the fluid into the submucosal layer T$_2$, the fluid "lifts" the polyp P (e.g., the injected fluid radially adjusts an orientation of the polyp P toward an axial center of the colon C relative to a noninjected portion of the colon tissue T). Once the injection procedure has been completed, the needle catheter is withdrawn 208 from the patient's colon C.

Prior to inserting 212 the distal portion $10b_D$ of the catheter portion 10b of the endoscopic catheter assembly 10 within a patient's colon, the endoscopic catheter assembly 10 may be optionally arranged in a stowed orientation 210 such that the first snare loop 116 and the second snare loop 18 are arranged within the passage 12 of the catheter portion 10b. The stowed orientation may result from initially arranging the first plunger 18 and the second plunger 20 relative the handle body 16 in an axially-retracted orientation that is axially closer to/in an axial direction toward the proximal portion $10a_P$ of the snare assembly portion 10a of the endoscopic catheter assembly 10. When the first plunger 18 and the second plunger 20 are arranged as described above, the first snare shaft 112 and the second snare shaft 114 are correspondingly axially retracted relative the catheter portion 10b thereby correspondingly axially retracting the first snare loop 116 and the second snare loop 118 such that first snare loop 116 and the second snare loop 118 are arranged in a collapsed orientation within the passage 12 of the catheter portion 10b.

The administrator may then insert 212 the distal portion $10b_D$ of the catheter portion 10b of the endoscopic catheter assembly 10 into the patient's colon C. Subsequently, the administrator navigates 214 the distal portion $10b_D$ of the catheter portion 10b of the endoscopic catheter assembly 10 within the colon C to the site of a polyp P extending from the colon tissue T. Although an exemplary method 200 for performing a polypectomy may include a step of injecting fluid as described above, steps 202-208 are not required for conducting a polypectomy procedure, and, as such, an exemplary method for performing a polypectomy procedure may, in some circumstances, only include the steps 210-216 for operating the endoscopic catheter assembly 10.

Once the distal portion $10b_D$ of the catheter portion 10b of the endoscopic catheter assembly 10 is navigated 214 to the site of the polyp P, the administrator may actuate 216 the snare assembly portion 10a of the endoscopic catheter assembly 10 for the purpose of removing 218 the polyp P from the colon tissue T. As will be described in the following disclosure, the actuating step 216 generally includes a variety of combinations of the administrator axially sliding the first plunger 18 and the second plunger 20 relative handle body 16 according to the direction of arrows X and X'.

Figure 20:
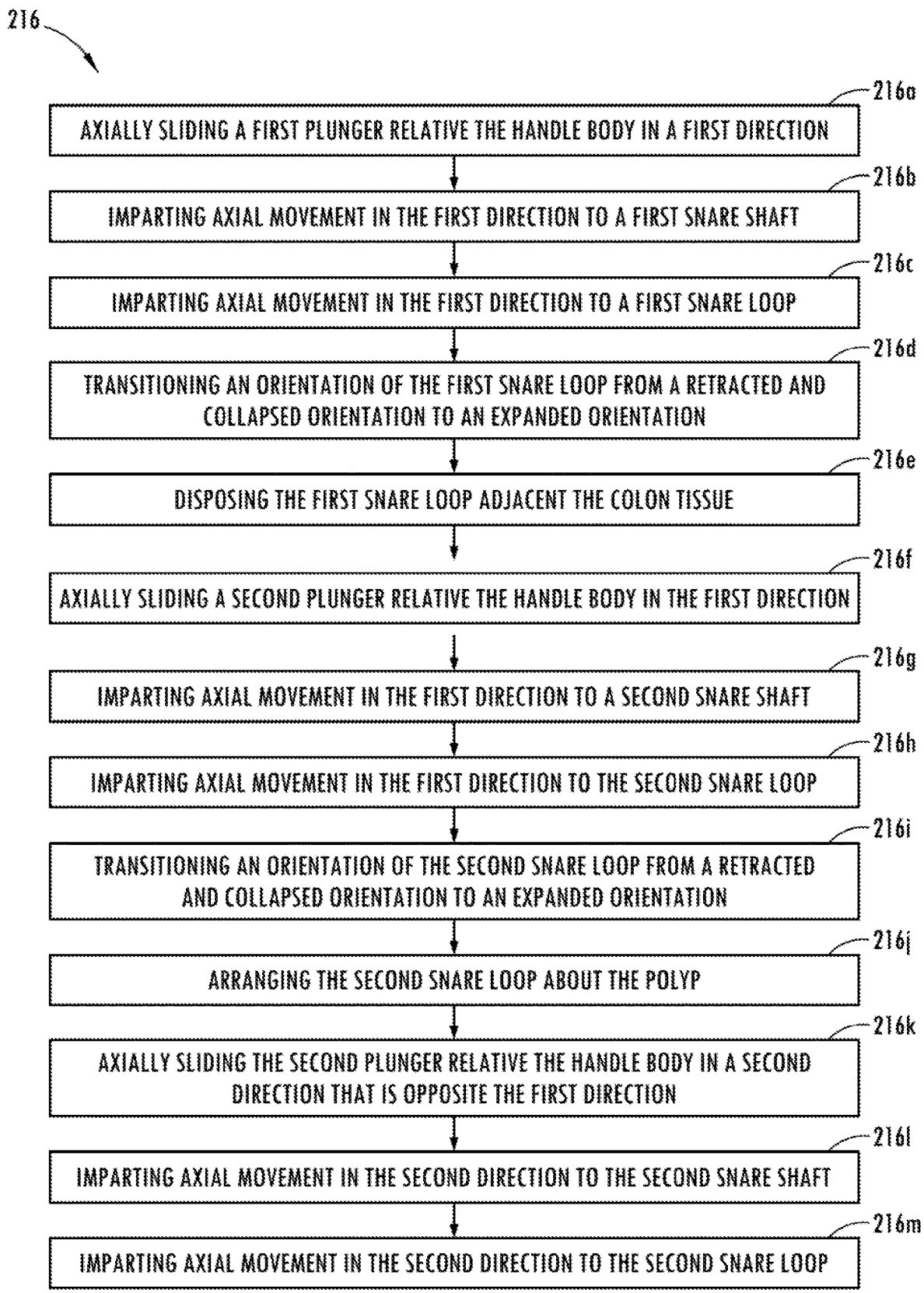
FIG. 20 is a flow diagram of an actuating step of the method of FIG. 19.

Referring to FIG. 20, in an example, the actuating step 216 may include axially sliding 216a (according to the direction of the arrow X) the first plunger 18 relative the handle body 16 for imparting axial movement 216b (according to the direction of the arrow X) of the first snare shaft 112 for imparting axial movement 216c (according to the direction of the arrow X) of the first snare loop 116 for transitioning an orientation 216d of the first snare loop 116 from a retracted and collapsed orientation within the passage 12 of the catheter portion 10b proximate the distal opening $12_{DO}$ formed by the distal portion $10b_D$ of the catheter portion 10b to a deployed and expanded orientation exterior of the passage 12. Once the first snare loop 116 is arranged exterior of the passage 12 of the catheter portion 10b, the administrator may radially adjust a spatial orientation of the first snare loop 116 within the patient's colon C for disposing 216e the outer surface 117 (which may include the colon tissue-engaging, frictional surface 119) of the first snare loop 116 adjacent the mucosa layer $T_1$ of the colon tissue T such that the first snare loop 116 substantially circumscribes the polyp P. By disposing 216e the first snare loop 116 adjacent the mucosa layer $T_1$ of the colon tissue T, the first snare loop 116 may functionally anchor (and radially expand to create tension) the distal portion $10a_D$ of the snare assembly portion 10a to the mucosa layer $T_1$ of the colon tissue T prior to removing the polyp P from the colon tissue T; furthermore, by disposing 216e the first snare loop 116 adjacent the mucosa layer $T_1$ of the colon tissue T, the colon tissue T may be flattened while stretching the submucosal layer $T_2$.

Once the first snare loop 116 is disposed 216e adjacent the mucosa layer $T_1$ of the colon tissue T, the actuating step 216 may further include axially sliding 216f (according to the direction of the arrow X) the second plunger 20 relative the handle body 16 for imparting axial movement 216g (according to the direction of the arrow X) of the second snare shaft 114 for imparting axial movement 216h (according to the direction of the arrow X) of the second snare loop 118 for transitioning an orientation 216i of the second snare loop 118 from a retracted and collapsed orientation within the passage 12 of the catheter portion 10b proximate the distal opening $12_{DO}$ formed by the distal portion $10b_D$ of the catheter portion 10b to a deployed and expanded orientation exterior of the passage 12. Referring to FIG. 21A, once the second snare loop 118 is arranged exterior of the passage 12 of the catheter portion 10b, the administrator may radially adjust a spatial orientation of the second snare loop 118 within the patient's colon C for arranging 216j the second snare loop 118 about the polyp P.

Referring to FIGS. 20 and 21B, once the second snare loop 118 is arranged about the polyp P, the administrator may axially slide 216k (according to the direction of arrow X') the second plunger 20 relative the handle body 16 for imparting axial movement 216l (according to the direction of the arrow X') of the second snare shaft 114 for imparting axial movement 216m (according to the direction of the arrow X' to create tension) to the second snare loop 118 for retracting the second snare loop 118 toward the distal opening $12_{DO}$ formed by the distal portion $10b_D$ of the catheter portion 10b. As seen in FIG. 21B, as the second snare loop 118 is retracted, the polyp P interferes with the imparted axial movement, and, as a result, as seen in FIG. 21C, the force of the second snare loop 118 applied to the polyp P results in the second snare loop 118 cutting/removing 218 (see, FIG. 19) the polyp P from the colon tissue T.

In some instances, the second snare loop 118 is in communication with a source of electricity (e.g., when the plug member 125 is inserted into the cautery device passage 32 such that the plug member 125 is interfaced with a portion of the length of the second snare shaft 114). The source of electricity provides a source of thermal energy to the second snare loop 118 for promoting the act of cutting the polyp P and cauterizing the colon tissue T as the polyp P is cut 218 from the colon tissue T. In other examples, the second snare loop 118 may not be in communication with a source of electricity, and, as a result, second snare loop 118 may operate as a "cold snare" when the polyp P is removed 218 from the colon tissue T. After the poly P is removed 218 from the colon tissue T, the above-described actuating steps 216a-216l may be performed in the reverse order such that the first snare loop 116 and the second snare loop 118 may be returned to the retracted and collapsed orientation within the passage 12 of the catheter portion 10b from the deployed and expanded orientation exterior of the passage 12 of the catheter portion 10b.

In the event that the administrator determines that the actuating steps 216a-216e related to the deployment of the first snare loop 116 described above are not sufficient for anchoring (and radially expand to create tension) the distal portion $10a_D$ of the snare assembly portion $10a$ to the mucosa layer $T_1$ of the colon tissue T prior to removing the polyp P from the colon tissue T (i.e., the shape of the polyp P and/or the location of the polyp P within the colon C impedes or does not permit the distal portion $10a_D$ of the snare assembly portion $10a$ to be anchored to the mucosa layer $T_1$ of the colon tissue T), the administrator may alternatively manipulate not only the first plunger 18 as described above at steps 216a-216e but also the second plunger 20 in a substantially similar manner in order to gather or further isolate the polyp P relative to surrounding colon tissue T. Once the polyp P has been sufficiently gathered or isolated, the administrator may conduct the actuating steps 216f-216m for removing/cutting the polyp P from the colon tissue T with the second snare loop 118.

In another example, in the event that the administrator determines that the actuating steps 216a-216e related to the deployment of the first snare loop 116 described above are not sufficient for anchoring (and radially expand to create tension) the distal portion $10a_D$ of the snare assembly portion $10a$ to the mucosa layer $T_1$ of the colon tissue T prior to removing the polyp P from the colon tissue T (i.e., the shape of the polyp P and/or the location of the polyp P within the colon C impedes or does not permit the distal portion $10a_D$ of the snare assembly portion $10a$ to be anchored to the mucosa layer $T_1$ of the colon tissue T), the administrator may alternatively manipulate the first plunger 18 in a manner after step 216e by axially sliding 216e' the first plunger 18 in a repeated back-and-forth manner according to the direction of the arrows X and X'. By axially sliding 216e' the first plunger 18 in the repeated back-and-forth manner, the first snare loop 116 may gather/further isolate the colon tissue T surrounding the polyp P prior to conducting the actuating steps 216f-216m for removing/cutting the polyp P from the colon tissue T with the second snare loop 118.

In yet another example, in the event that the administrator determines that the actuating steps 216a-216e related to the deployment of the first snare loop 116 described above are not sufficient for anchoring the distal portion $10a_D$ of the snare assembly portion $10a$ to the mucosa layer $T_1$ of the colon tissue T prior to removing the polyp P from the colon tissue T (i.e., the shape of the polyp P and/or the location of the polyp P within the colon C impedes or does not permit the distal portion $10a_D$ of the snare assembly portion $10a$ to be anchored to the mucosa layer $T_1$ of the colon tissue T), the administrator may alternatively manipulate both of the first plunger 18 and the second plunger 20 in a manner after step 216e by axially sliding 216e" both of the first plunger 18 and the second plunger 20 in a repeated back-and-forth manner according to the direction of the arrows X and X'. By axially sliding 216e" both of the first plunger 18 and the second plunger 20 in the repeated back-and-forth manner, the first snare loop 116 and the second snare loop 118 may gather/further isolate the colon tissue T surrounding the polyp P prior to conducting the actuating steps 216f-216m for removing/cutting the polyp P from the colon tissue T with the second snare loop 118.

Figure 22A:
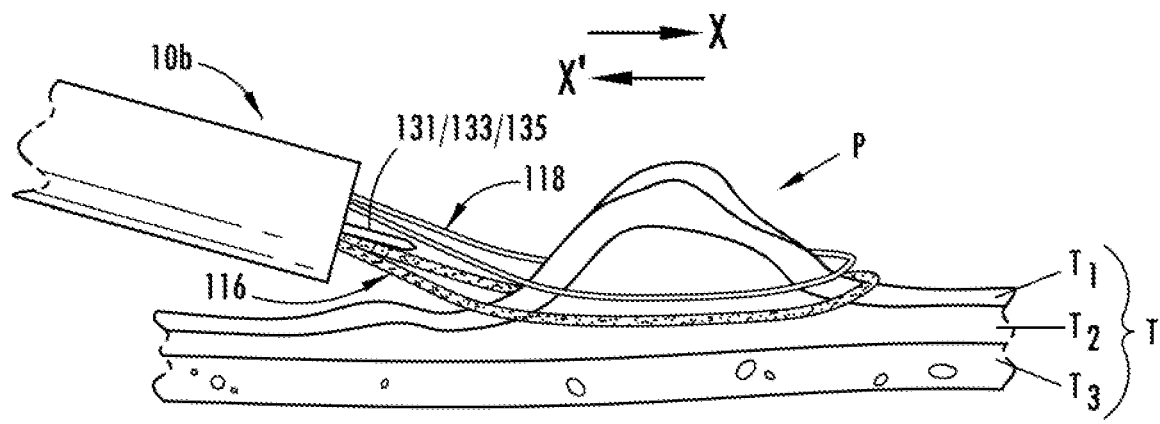
FIGS. 22A-22C are views of a distal portion of an exemplary snare subassembly portion and a distal portion of an exemplary catheter portion of an exemplary endoscopic catheter assembly conducting a polypectomy procedure.
Figure 22B:
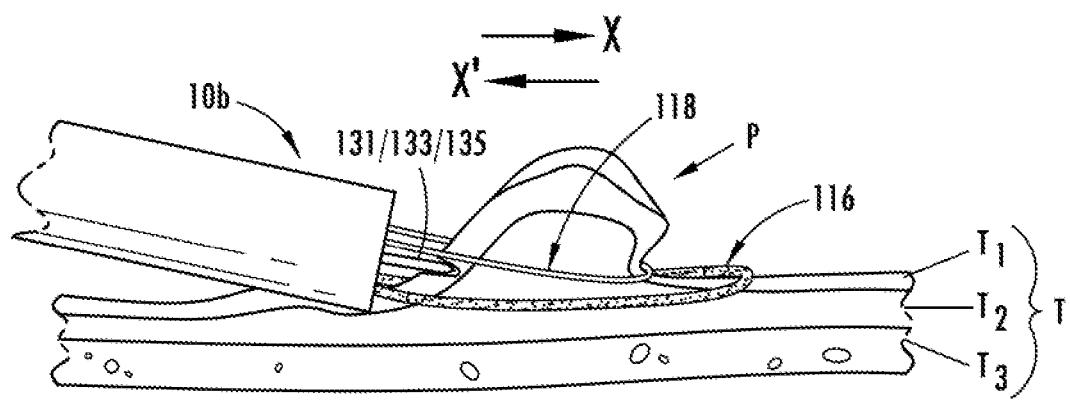
Figure 22C:
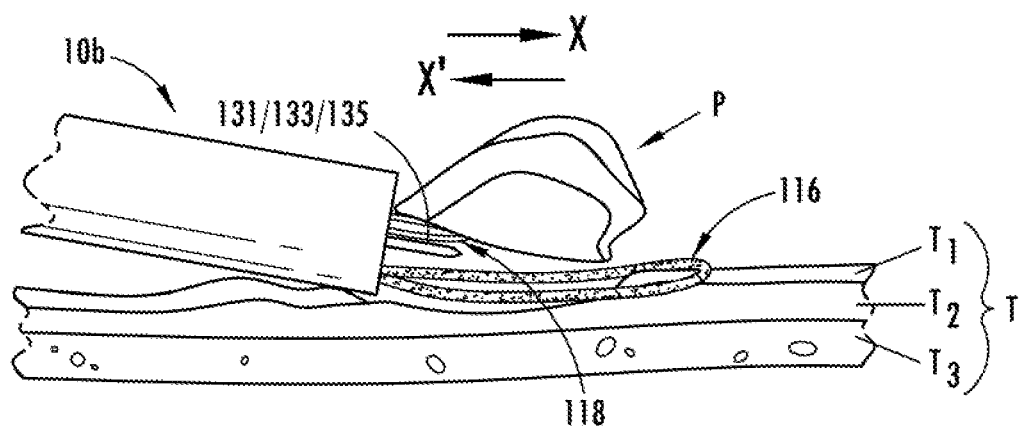

Although some implementations of a method 200 including steps (see, e.g., steps 210-216) for operating the endoscopic catheter assembly 10 and/or performing a polypectomy procedure (see, e.g., steps 202-218) may be conducted in the context as described above at FIGS. 21A-21C, other structural implementations of an endoscopic catheter assembly 10 including a cutting surface profile (see, e.g., blade portions 131, 133, 135 described above) may be utilized in conjunction with the snare loops 116, 118 as described above. For example, as seen in FIGS. 22A-22C, as an operator manipulates the endoscopic catheter assembly 10, the blade portion 131/133/135 may cut through the polyp P alone, or, alternatively, in conjunction with the second snare loop 118.

Figure 23A:
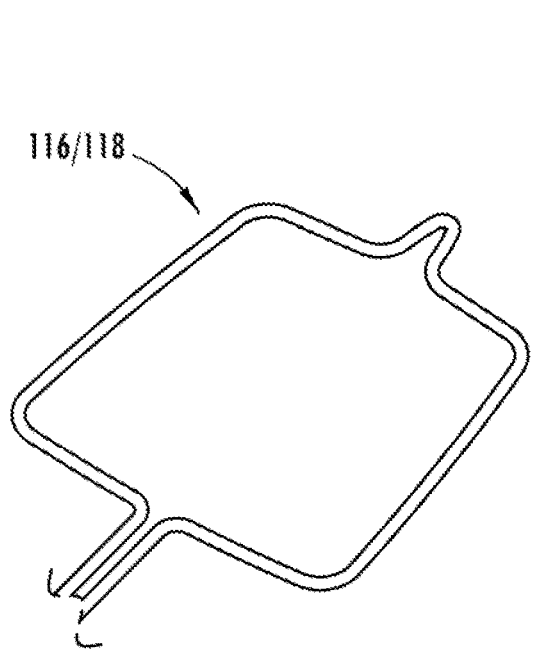
FIGS. 23A-23B are views of exemplary snare loops that may be incorporated into the design of any endoscopic catheter assembly described in the present disclosure.
Figure 23B:
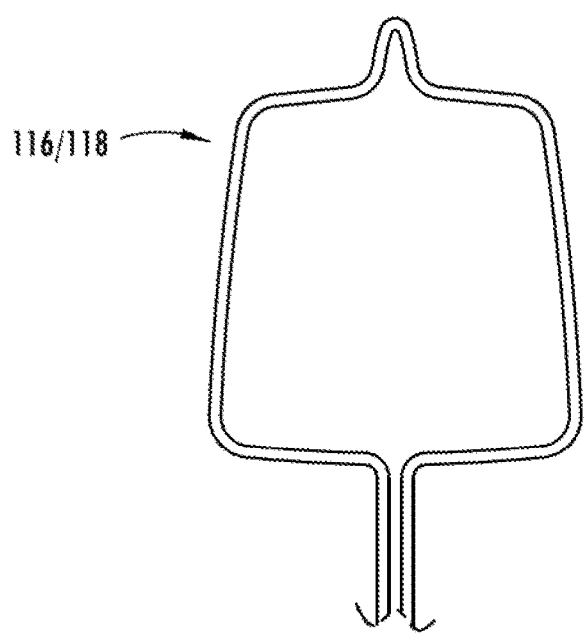
Figure 24A:
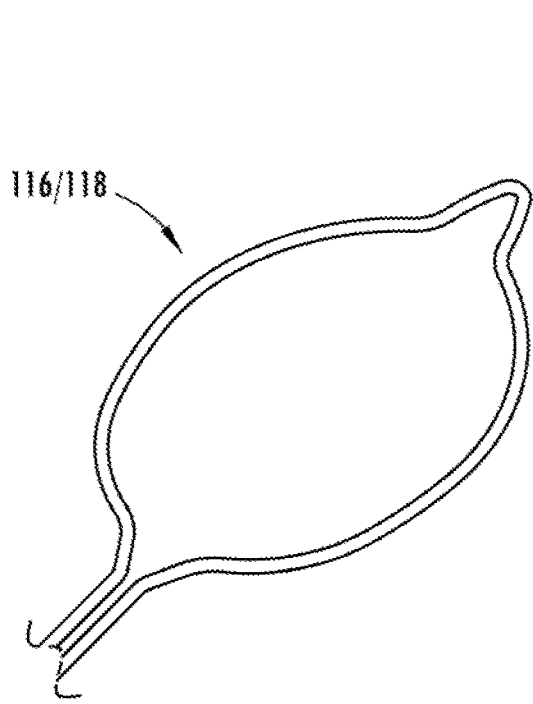
FIGS. 24A-24B are views of exemplary snare loops that may be incorporated into the design of any endoscopic catheter assembly described in the present disclosure.
Figure 24B:
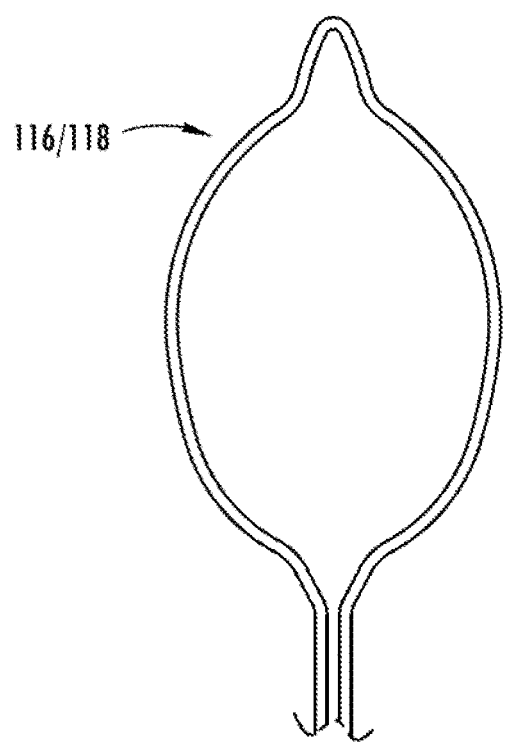
Figures 25A, 25B:
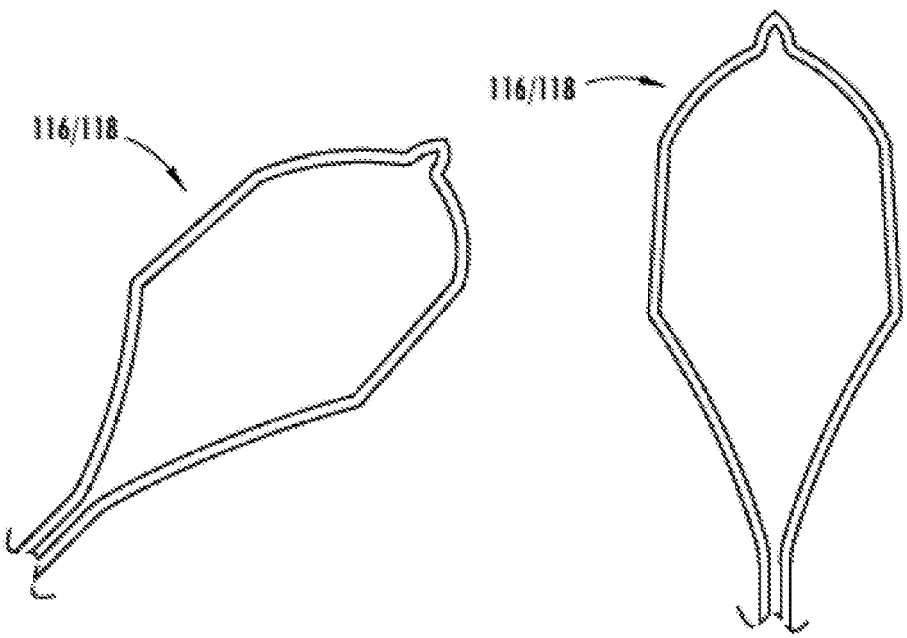
FIGS. 25A-25B are views of exemplary snare loops that may be incorporated into the design of any endoscopic catheter assembly described in the present disclosure.
Figures 26A, 26B:
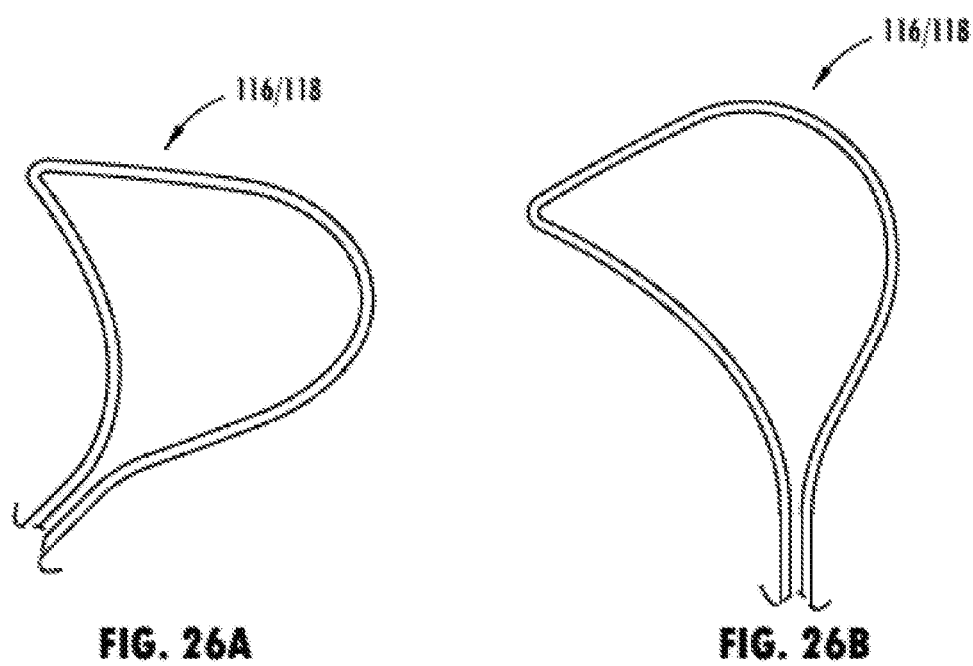
FIGS. 26A-26B are views of exemplary snare loops that may be incorporated into the design of any endoscopic catheter assembly described in the present disclosure.

Furthermore, although the above described exemplary implementations illustrate the first snare loop 116 and the second snare loops 118 have a tear-drop shape, the invention is not limited to a particular shape or configuration. For example, referring to FIGS. 23A-23B, 24A-24B, 25A-25B and 26A-26B, each of the first snare loop 116 and the second snare loops 118 may take the form of any shape or geometry including, for example: a square shape geometry (see, e.g., FIGS. 23A-23B), a circular shape geometry (see, e.g., FIGS. 24A-24B), a duck-bill shape geometry (see, e.g., FIGS. 25A-25B) or a circular-curved shape geometry (see, e.g., FIGS. 26A-26B).

A number of implementations have been described. Nevertheless, it will be understood that various modifications may be made without departing from the spirit and scope of the disclosure. Accordingly, other implementations are within the scope of the following claims. For example, the actions recited in the claims can be performed in a different order and still achieve desirable results.

What is claimed is:

1. An endoscopic catheter assembly, comprising:
 a catheter portion having a proximal portion and a distal portion, wherein the catheter portion includes a tube-shaped body defining a passage extending therethrough, wherein a radial wall extends across the passage formed by the catheter portion thereby connecting diametrically-opposing portions of an inner surface of the tube-shaped body defining the passage for bifurcating at least a portion of a length of the passage proximate a distal opening formed by the distal portion of the catheter portion into a first passage portion and a second passage portion, wherein the radial wall includes a cutting surface having a sharp cutting surface profile, wherein the first passage portion contains and guides:
 a portion of a length of a first snare shaft proximate a distal end of the first snare shaft; and
 a first snare loop connected to the distal end of the first snare shaft, wherein the second passage portion contains and guides:
 a portion of a length of a second snare shaft proximate a distal end of the second snare shaft; and
 a second snare loop connected to the distal end of the second snare shaft.

2. A method for removing pathogenic tissue from a body of a patient, said method comprising the steps of:
 providing an endoscope including a catheter portion having a proximal portion and a distal portion, wherein the catheter portion includes a tube-shaped body defining a passage extending there-through, wherein a radial wall extends across the passage formed by the catheter portion thereby connecting diametrically-opposing portions of an inner surface of the tube-shaped body defining the passage for bifurcating at least a portion of a length of the passage proximate a distal opening formed by the distal portion of the catheter portion into a first passage portion and a second passage portion, wherein the radial wall includes a cutting surface having a sharp cutting surface profile, wherein the catheter portion is suitable for performing an endoscopic procedure on the patient, wherein the catheter portion is sized for removing pathogenic tissue and is sized and dimensioned for insertion into the endoscope;

inserting the endoscope into the body of the patient and locating the pathogenic tissue to be removed with the endoscope;

arranging the distal portion of the catheter portion proximate the pathogenic tissue;

extending a first snare loop of the catheter portion from a retracted and collapsed orientation to an extended orientation for forming a hoop that is dimensioned to capture the pathogenic tissue;

manipulating the first snare loop to substantially flatten surrounding healthy tissue;

activating a cable trigger for drawing the first snare loop proximally relative to the catheter portion while being arranged around the pathogenic tissue and healthy tissue thereby raising the pathogenic tissue relative to the healthy tissue;

extending a second snare loop of the catheter portion from a retracted and collapsed orientation to an extended orientation for forming a hoop that is dimensioned to capture the pathogenic tissue at an interface between the pathogenic tissue and the healthy tissue;

manipulating the second snare loop for drawing and tightening around the pathogenic tissue for severing the pathogenic tissue from the healthy tissue surrounding the pathogenic tissue.

3. The method of claim 2, wherein the pathogenic tissue is a neoplasm, a cancer, a solid tumor, a metastatic cancer, a cancerous lesion, an inflamed tissue, a precancerous tissue, a necrotic tissue, an infected tissue, a calcified tissue, or combinations thereof.

* * * * *